US009725734B2

(12) United States Patent
Stover et al.

(10) Patent No.: US 9,725,734 B2
(45) Date of Patent: Aug. 8, 2017

(54) THIONIN-D4E1 CHIMERIC PROTEIN PROTECTS PLANTS AGAINST BACTERIAL INFECTIONS

(71) Applicants: The United States of America, as represented by the Secretary of Agriculture, Washington, DC (US); Los Alamos National Security, LLC, Los Alamos, NM (US)

(72) Inventors: Eddie W Stover, Fort Pierce, FL (US); Goutam Gupta, Santa Fe, NM (US); Guixia Hao, Fort Pierce, FL (US)

(73) Assignees: The United States of America, as represented by the Secretary of Agriculture, Washington, DC (US); Los Alamos National Security, LLC, Los Alamos, NM (US)

(*) Notice: Subject to any disclaimer, the term of this patent is extended or adjusted under 35 U.S.C. 154(b) by 0 days.

(21) Appl. No.: 14/691,780

(22) Filed: Apr. 21, 2015

(65) Prior Publication Data

US 2016/0312241 A1 Oct. 27, 2016

(51) Int. Cl.
*C12N 15/82* (2006.01)
*C07K 7/08* (2006.01)
*C07K 14/415* (2006.01)

(52) U.S. Cl.
CPC ............ *C12N 15/8281* (2013.01); *C07K 7/08* (2013.01); *C07K 14/415* (2013.01); *C07K 2319/00* (2013.01)

(58) Field of Classification Search
None
See application file for complete search history.

(56) References Cited

PUBLICATIONS

Alan, A.R. et al., "Expression of a magainin-type antimicrobial peptide gene (MSI-99) in tomato enhances resistance to bacterial speck disease", (2004), Plant Cell Report 22:388-396.
Attilio, Lisia Borges et al., "Genetic transformation of sweet oranges with the D4E1 gene driven by the AtPP2 promoter", (2013), Pesq. agropec.bras., Brasilia, 48(7):741-747.
Ballweber, L.M. et al., "In Vitro Microbicidal Activities of Cecropin Peptides D2A21 and D4E1 and Gel Formulations Containing 0.1 to 2% D2A21 against Chlamydia trachomatis", (2002), Antimicrobial Agents and Chemotherapy, 46(1):34-41.
Bohlmann, Holger et al., "Leaf-specific thionins of barley—a novel class of cell wall proteins toxic to plant-pathogenic fungi and possibly involved in the defence mechanism of plants", (1988), The EMBO Journal, 7(6):1559-1565.
Broekaert, Willem F. et al., "Antimicrobial Peptides from Plants", (1997), Critical Reviews in Plant Sciences, 16(3):297-323.
Carmona, Maria Jose et al., "Expression of the a-thionin gene from barley in tobacco confers enhanced resistance to bacterial pathogens", (1993), The Plant Journal, 3(3):457-462.
Cary, Jeffrey W. et al., "Transgenic expression of a gene encoding a synthetic antimicrobial peptide results in inhibition of fungal growth in vitro and in planta", (2000), Plant Science, 154:171-181.
Cavallarin, Laura et al., "Cecropin A-Derived Peptides Are Potent Inhibitors of Fungal Plant Pathogens", (1998), Molecular Plant-Microbe Interations, 11(3):218-227.
Chakrabarti, A. et al., "MSI-99, a magainin analogue, imparts enhanced disease resistance in transgenic tobacco and banana", (2003), Planta, 216:587-596.
Coca, Maria et al., "Enhanced resistance to the rice blast fungus Magnaporthe grisea conferred by expression of a cecropin A gene in transgenic rice", (2006), Planta, 223:392-406.
Dandekar, Abhaya M. et al., "An engineered innate immune defense protects grapevines from Pierce disease", (2012), PNAS, 199(10):3721-3725.
Delucca, Anthony J. et al., "Fungicidal Activity of Cecropin A", (1997), Antimicrobial Agents and Chemotherapy, 41(2):481-483.
Delucca, Anthony J. et al., "Antifungal Peptides: Novel Therapeutic Compounds against Emerging Pathogens", (1999), Antimicrobial Agents and Chemotherapy, 43(1):1-11.
Delucca, Anthony J. et al., "Fungicidal properties, sterol binding, and proteolytic resistance of the synthetic peptide D4E1", (1998), Can. Journal Microbiology, 44:514-520.
Epple, Petra et al., "Overexpression of an Endogenous Thionin Enhances Resistance of Arabidopsis against Fusarium oxysporum", (1997), The Plant Cell, 9:509-520.
Hao, Guixia et al., "Production of Transgenic Citrus Resistant to Citrus Canker and Huanglongbing Diseases", (2014), Slide Presentation presented at American Society for Horticultural Science.
Huang, Y. et al., "Expression of an Engineered Cecropin Gene Cassette in Transgenic Tobacco Plants Confers Disease Resistance to *Pseudomonas syringae* pv. tabaci", (1997), Molecular Plant Pathology, 87(5):494-499.
Imamura, Tomohiro et al., "Acquired resistance to the rice blast in transgenic rice accumulating the antimicrobial peptide thanatin", (2010), Transgenic Research, 19:415-424.
Iwai, Takayoshi et al., "Enhanced Resistance to Seed-Transmitted Bacterial Diseases in Transgenic Rice Plants Overproducing an Oat Cell-Wall-Bound Thionin", (2002), Molecular Plant-Microbe Interactions, 15(6):515-521.
Jaynes, Jesse M. et a;., "Expression of a Cecropin B lytic peptide analog in tobacco confers enhanced resistance to bacterial wilt Pseudomonas solanacearum transgenic caused by", (1993), Plant Science, 89:43-53.

(Continued)

*Primary Examiner* — Medina A Ibrahim
(74) *Attorney, Agent, or Firm* — David L. Marks; John D. Fado

(57) ABSTRACT

The generation of a chimeric protein containing a first domain encoding either a pro-thionon or thionin, a second domain encoding D4E1 or pro-D4E1, and a third domain encoding a peptide linker located between the first domain and second domain is described. Either the first domain or the second domain is located at the amino terminal of the chimeric protein and the other domain (second domain or first domain, respectively) is located at the carboxyl terminal. The chimeric protein has antibacterial activity. Genetically altered plants and their progeny expressing a polynucleotide encoding the chimeric protein resist diseases caused by bacteria.

16 Claims, 6 Drawing Sheets

(56) References Cited

PUBLICATIONS

Jung, Yu-Jin et al., "Enhanced resistance to bacterial and fungal pathogens by overexpression of a human cathelicidin antimicrobial peptide (hCAP18/LL-37) in Chinese cabbage", (2012), Plant Biotechnology Report, 6:39-46.
Lee, Sung Chul et al., "Involvement of the Pepper Antimicrobial Protein CaAMP1 Gene in Broad Spectrum Disease Resistance1[C][OA]", (2008), Plant Phisiology, 148:1004-1020.
Lopez-Garcia, Belen et al., "Identification of Novel Hexapeptides Bioactive against Phytopathogenic Fungi through Screening of a Synthetic Peptide Combinatorial Library", (2002), Applied and Environmental Microbiology, 68 (5):2453-2460.
Lopez-Garcia, Belen et al., "Identification and Characterization of a Hexapeptide with Activity Against Phytopathogenic Fungi That Cause Postharvest Decay in Fruits" (2000), Molecular Plant-Microbe Interactions, 13 (8):837-846.
Marcos, Jose F. et al., "Identification and Rational Design of Novel Antimicrobial Peptides for Plant Protection", (2008), Annual Review Phytopathology, 46:273-301.
Mentag, R. et al., "Bacterial disease resistance of transgenic hybrid poplar expressing the synthetic antimicrobial peptide D4E1", (2003), Tree Physiology, 23:405-411.
Molina, Antonio et al., "Inhibition of bacterial and fungal plant pathogens by thionins of types I and II", (1993), Plant Science, 92(2):169-177.
Monrac, Sylvie et al., "De novo designed cyclic cationic peptides as inhibitors of plant pathogenic bacteria", (2006), Peptides, 27:2567-2574.
Monrac, Sylvie et al., "Improvement of cyclic decapeptides against plant pathogenic bacteria using a combinatorial chemistry approach", (2006), Peptides, 27:2575-2584.
Montesinos, Emilio, "Antimicrobial peptides and plant disease control", (2007), FEMS Microbiol Lett, 270:1-11.
Muramoto, Nobuhiko et al., "Transgenic sweet potato expressing thionin from barley gives resistance to black rot disease caused by Ceratocystis fimbriata in leaves and storage roots", (2012) Plant Cell Rep, 31:987-997.
Oard, Svetlana V., "Deciphering a mechanism of membrane permeabilization by α-hordothionin peptide", (2011), Biochimica et Biophysica Acta, 1737-1745.
Osusky, Milan et al., "Transgenic potatoes expressing a novel cationic peptide are resistant to late blight and pink rot", (2004), Transgenic Research, 13:181-190.
Pelegrini, Patrica B. and Franco, Octavio L., "Plant y-thionins: Novel insights on the mechanism of action of a multi-functional class of defense proteins", (2005), The International Journal of Biochemistry & Cell Biology, 37:2239-2253.
Rajasekaran, Kanniah et al., "Broad-Spectrum Antimicrobial Activity in vitro of the Synthetic Peptide D4E1", (2001), Journal of Agricultural and Food Chemistry, 49:2799-2803.
Rajasekaran, Kanniah et al., "Disease resistance conferred by the expression of a gene encoding a synthetic peptide in transgenic cotton (*Gossypium hirsutum* L.) plants", (2005), Plant Biotechnology Journal, 3:545-554.
Reynoird, J.P. et al., "First evidence for improved resistance to fire blight in transgenic pear expressing the attacin E gene from Hyalophora cecropia", (1999), Plant Science, 149:23-31.
Stover, ED et al., "Screening Antimicrobial Peptides In Vitro for Use in Developing Transgenic Citrus Resistant to Huanglongbing and Citrus Canker", (2013), Journal of the American Society for Horticultural Science, 138 (2):142-148.

FIG. 1

| | | | | | | | |
|---|---|---|---|---|---|---|---|
| Tobacco | MANSMRFFAT | VLLIALLVTA | TEMGPMTIAE | ARTCESQSHR | FKGPCSRDSN | | SEQ ID NO: 4 |
| Citrus | MERSVRLFST | VLLVLLLL-A | SEMG-LRAAE | ARICESQSHR | FKGPCVSKSN | | SEQ ID NO: 16 |
| Optimized | MANSMRFFAT | VLLIALLVTA | TEMGPMTIAE | ARTCESQSHR | FKGPCSRDSN | | SEQ ID NO: 6 |
| | ** * * * | ** ** | * **** | * | *** | | |
| Tobacco | CATVCLTEGF | SGGDCRGFRR | RCFCTRPC-- | --- | | | SEQ ID NO: 4 |
| Citrus | CAAVCQTEGF | HGGHCRGFRR | RCFCTKRC-- | --- | | | SEQ ID NO: 16 |
| Optimized | CATVCLTEGF | SGGDCRGFRR | RCRCTRPCVF | DEK | | | SEQ ID NO: 6 |
| | * * | * * | * ** ** | *** | | | |

FIG. 2

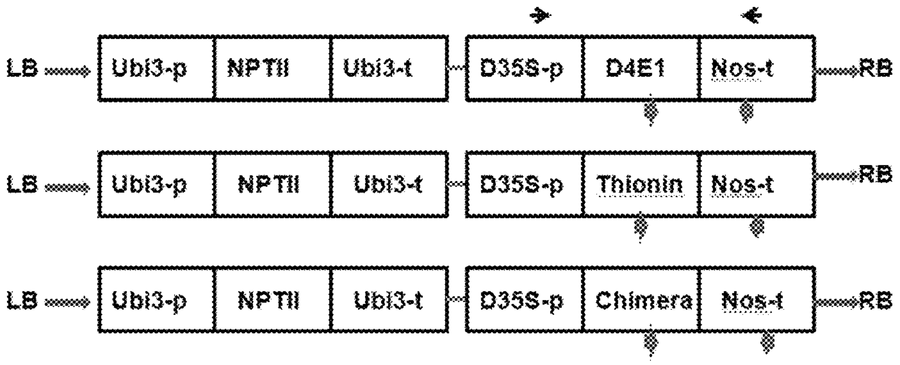

Optimized pro-thionin-linker 1-D4E1 Nontransformed D4E1

SEQUENCE LISTING

```
<160> NUMBER OF SEQ ID NOS: 78

<210> SEQ ID NO 1
<211> LENGTH: 57
<212> TYPE: DNA
<213> ORGANISM: Artificial Sequence
<220> FEATURE:
<223> OTHER INFORMATION: D4E1 coding sequence

<400> SEQUENCE: 1

atgtttaagc ttcgtgcaaa aatcaaggtg aggttgagag ctaagattaa actctga        57


<210> SEQ ID NO 2
<211> LENGTH: 17
<212> TYPE: PRT
<213> ORGANISM: Artificial Sequence
<220> FEATURE:
<223> OTHER INFORMATION: D4E1

<400> SEQUENCE: 2

Phe Lys Leu Arg Ala Lys Ile Lys Val Arg Leu Arg Ala Lys Ile Lys
1               5                   10                  15

Leu


<210> SEQ ID NO 3
<211> LENGTH: 237
<212> TYPE: DNA
<213> ORGANISM: Nicotiana benthamiana

<400> SEQUENCE: 3

atggcaaact ccatgcgctt ctttgcaact gtgttactta tagcattgct tgtcacggct      60

accgagatgg gaccaatgac aattgcagag gcaagaactt gtgagtccca gagccaccgt     120

ttcaagggac catgctcaag agatagcaac tgtgccaccg tttgtctgac cgaaggattt     180

tccggtggcg actgccgtgg attccgccgc cgttgtttct gtaccaggcc ttgctaa        237


<210> SEQ ID NO 4
<211> LENGTH: 78
<212> TYPE: PRT
<213> ORGANISM: Nicotiana benthamiana

<400> SEQUENCE: 4

Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Arg
            20                  25                  30

Thr Cys Glu Ser Gln Ser His Arg Phe Lys Gly Pro Cys Ser Arg Asp
        35                  40                  45

Ser Asn Cys Ala Thr Val Cys Leu Thr Glu Gly Phe Ser Gly Gly Asp
    50                  55                  60

Cys Arg Gly Phe Arg Arg Arg Cys Phe Cys Thr Arg Pro Cys
65                  70                  75
```

-continued

<210> SEQ ID NO 5
<211> LENGTH: 252
<212> TYPE: DNA
<213> ORGANISM: Artificial Sequence
<220> FEATURE:
<223> OTHER INFORMATION: optimized pro-thionin coding sequence

<400> SEQUENCE: 5
atggcaaact cgatgaggtt ctttgctaca gttttattga tcgcacttct tgtgaccgct 60
acagagatgg gtccgatgac catagctgaa gccagaactt gtgagtctca atctcatagg 120
tttaaaggtc cttgtagtcg cgattccaat tgtgcgacag tatgtctcac ggaagggttt 180
tcaggcggtg actgccgagg atttcgccgt agatgcagat gcactcggcc atgtgttttc 240
gatgaaaaat ga 252

<210> SEQ ID NO 6
<211> LENGTH: 83
<212> TYPE: PRT
<213> ORGANISM: Artificial Sequence
<220> FEATURE:
<223> OTHER INFORMATION: optimized pro-thionin

<400> SEQUENCE: 6

Met Ala Asn Ser Met Arg Phe Phe Ala Thr Val Leu Leu Ile Ala Leu
1 5 10 15

Leu Val Thr Ala Thr Glu Met Gly Pro Met Thr Ile Ala Glu Ala Arg
20 25 30

Thr Cys Glu Ser Gln Ser His Arg Phe Lys Gly Pro Cys Ser Arg Asp
35 40 45

Ser Asn Cys Ala Thr Val Cys Leu Thr Glu Gly Phe Ser Gly Gly Asp
50 55 60

Cys Arg Gly Phe Arg Arg Arg Cys Arg Cys Thr Arg Pro Cys Val Phe
65 70 75 80

Asp Glu Lys

<210> SEQ ID NO 7
<211> LENGTH: 324
<212> TYPE: DNA
<213> ORGANISM: Artificial Sequence
<220> FEATURE:
<223> OTHER INFORMATION: optimized pro-thionin-linker 1-D4E1 coding
sequence

<400> SEQUENCE: 7
atggcaaact cgatgaggtt ctttgctaca gttttattga tcgcacttct tgtgaccgct 60
acagagatgg gtccgatgac catagctgaa gccagaactt gtgagtctca atctcatagg 120
tttaaaggtc cttgtagtcg cgattccaat tgtgcgacag tatgtctcac ggaagggttt 180
tcaggcggtg actgccgagg atttcgccgt agatgcagat gcactcggcc atgtgttttc 240
gatgaaaaag gaagcactgc tccacctgca ttcaaactac gtgctaagat taaggtcaga 300
ctgagagcga agattaagtt gtga 324

<210> SEQ ID NO 8
<211> LENGTH: 107
<212> TYPE: PRT
<213> ORGANISM: Artificial Sequence
<220> FEATURE:
<223> OTHER INFORMATION: optimized pro-thionin-linker 1-D4E1

<400> SEQUENCE: 8

```
Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Arg
            20                  25                  30

Thr Cys Glu Ser Gln Ser His Arg Phe Lys Gly Pro Cys Ser Arg Asp
        35                  40                  45

Ser Asn Cys Ala Thr Val Cys Leu Thr Glu Gly Phe Ser Gly Gly Asp
    50                  55                  60

Cys Arg Gly Phe Arg Arg Arg Cys Arg Cys Thr Arg Pro Cys Val Phe
65                  70                  75                  80

Asp Glu Lys Gly Ser Thr Ala Pro Pro Ala Phe Lys Leu Arg Ala Lys
                85                  90                  95

Ile Lys Val Arg Leu Arg Ala Lys Ile Lys Leu
            100                 105


<210> SEQ ID NO 9
<211> LENGTH: 21
<212> TYPE: DNA
<213> ORGANISM: Artificial Sequence
<220> FEATURE:
<223> OTHER INFORMATION: DNA encoding linker 1

<400> SEQUENCE: 9

tcaggcggtg actgccgagg a                                                21


<210> SEQ ID NO 10
<211> LENGTH: 7
<212> TYPE: PRT
<213> ORGANISM: Artificial Sequence
<220> FEATURE:
<223> OTHER INFORMATION: linker 1 peptide

<400> SEQUENCE: 10

Gly Ser Thr Ala Pro Pro Ala
1               5


<210> SEQ ID NO 11
<211> LENGTH: 92
<212> TYPE: DNA
<213> ORGANISM: Nicotiana benthamiana

<400> SEQUENCE: 11

atggcaaact cgatgaggtt ctttgctaca gttttattga tcgcacttct tgtgaccgct     60

acagagatgg gtccgatgac catagctgaa gc                                    92


<210> SEQ ID NO 12
<211> LENGTH: 31
<212> TYPE: PRT
<213> ORGANISM: Nicotiana benthamiana

<400> SEQUENCE: 12

Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala
            20                  25                  30


<210> SEQ ID NO 13
<211> LENGTH: 156
<212> TYPE: DNA
<213> ORGANISM: Artificial Sequence
<220> FEATURE:
```

<223> OTHER INFORMATION: optimized thionin coding sequence

<400> SEQUENCE: 13
agaacttgtg agtctcaatc tcataggttt aaaggtcctt gtagtcgcga ttccaattgt 60
gcgacagtat gtctcacgga agggttttca ggcggtgact gccgaggatt tcgccgtaga 120
tgcagatgca ctcggccatg tgttttcgat gaaaaa 156

<210> SEQ ID NO 14
<211> LENGTH: 52
<212> TYPE: PRT
<213> ORGANISM: Artificial Sequence
<220> FEATURE:
<223> OTHER INFORMATION: optimized thionin

<400> SEQUENCE: 14

Arg Thr Cys Glu Ser Gln Ser His Arg Phe Lys Gly Pro Cys Ser Arg
1 5 10 15

Asp Ser Asn Cys Ala Thr Val Cys Leu Thr Glu Gly Phe Ser Gly Gly
20 25 30

Asp Cys Arg Gly Phe Arg Arg Arg Cys Arg Cys Thr Arg Pro Cys Val
35 40 45

Phe Asp Glu Lys
50

<210> SEQ ID NO 15
<211> LENGTH: 231
<212> TYPE: DNA
<213> ORGANISM: Citrus sinensis

<400> SEQUENCE: 15
atggagcgct cagtgcgttt attttcaact gttctacttg tgctgctgct tcttgccagt 60
gaaatggggc tgagggcggc agaagctagg atatgcgagt ctcagagtca ccggttcaag 120
gggccatgtg tgagtaagag caactgtgct gctgtttgcc aaactgaagg gttccacggt 180
ggccactgcc gtggattccg tcgtcgatgc ttttgcacta aaagatgtta a 231

<210> SEQ ID NO 16
<211> LENGTH: 76
<212> TYPE: PRT
<213> ORGANISM: Citrus sinensis

<400> SEQUENCE: 16

Met Glu Arg Ser Val Arg Leu Phe Ser Thr Val Leu Leu Val Leu Leu
1 5 10 15

Leu Leu Ala Ser Glu Met Gly Leu Arg Ala Ala Glu Ala Arg Ile Cys
20 25 30

Glu Ser Gln Ser His Arg Phe Lys Gly Pro Cys Val Ser Lys Ser Asn
35 40 45

Cys Ala Ala Val Cys Gln Thr Glu Gly Phe His Gly Gly His Cys Arg
50 55 60

Gly Phe Arg Arg Arg Cys Phe Cys Thr Lys Arg Cys
65 70 75

<210> SEQ ID NO 17
<211> LENGTH: 231
<212> TYPE: DNA
<213> ORGANISM: Artificial Sequence
<220> FEATURE:
<223> OTHER INFORMATION: optimized thionin-linker 1-D4E1 coding sequence

<400> SEQUENCE: 17
agaacttgtg agtctcaatc tcataggttt aaaggtcctt gtagtcgcga ttccaattgt 60
gcgacagtat gtctcacgga agggttttca ggcggtgact gccgaggatt tcgccgtaga 120
tgcagatgca ctcggccatg tgttttcgat gaaaaaggaa gcactgctcc acctgcattc 180
aaactacgtg ctaagattaa ggtcagactg agagcgaaga ttaagttgtg a 231

<210> SEQ ID NO 18
<211> LENGTH: 76
<212> TYPE: PRT
<213> ORGANISM: Artificial Sequence
<220> FEATURE:
<223> OTHER INFORMATION: optimized thionin-linker 1-D4E1

<400> SEQUENCE: 18

Arg Thr Cys Glu Ser Gln Ser His Arg Phe Lys Gly Pro Cys Ser Arg
1 5 10 15

Asp Ser Asn Cys Ala Thr Val Cys Leu Thr Glu Gly Phe Ser Gly Gly
20 25 30

Asp Cys Arg Gly Phe Arg Arg Arg Cys Arg Cys Thr Arg Pro Cys Val
35 40 45

Phe Asp Glu Lys Gly Ser Thr Ala Pro Pro Ala Phe Lys Leu Arg Ala
50 55 60

Lys Ile Lys Val Arg Leu Arg Ala Lys Ile Lys Leu
65 70 75

<210> SEQ ID NO 19
<211> LENGTH: 145
<212> TYPE: DNA
<213> ORGANISM: Nicotiana benthamiana

<400> SEQUENCE: 19
aagaacttgt gagtcccaga gccaccgttt caagggacca tgctcaagag atagcaactg 60
tgccaccgtt tgtctgaccg aaggattttc cggtggcgac tgccgtggat tccgccgccg 120
ttgtttctgt accaggcctt gctaa 145

<210> SEQ ID NO 20
<211> LENGTH: 47
<212> TYPE: PRT
<213> ORGANISM: Nicotiana benthamiana

<400> SEQUENCE: 20

Arg Thr Cys Glu Ser Gln Ser His Arg Phe Lys Gly Pro Cys Ser Arg
1 5 10 15

Asp Ser Asn Cys Ala Thr Val Cys Leu Thr Glu Gly Phe Ser Gly Gly
20 25 30

Asp Cys Arg Gly Phe Arg Arg Arg Cys Phe Cys Thr Arg Pro Cys
35 40 45

<210> SEQ ID NO 21
<211> LENGTH: 144
<212> TYPE: DNA
<213> ORGANISM: Citrus sinensis

<400> SEQUENCE: 21
aggatatgcg agtctcagag tcaccggttc aaggggccat gtgtgagtaa gagcaactgt 60
gctgctgttt gccaaactga agggttccac ggtggccact gccgtggatt ccgtcgtcga 120
tgcttttgca ctaaaagatg ttaa 144

<210> SEQ ID NO 22
<211> LENGTH: 47
<212> TYPE: PRT
<213> ORGANISM: Citrus sinensis

<400> SEQUENCE: 22

```
Arg Ile Cys Glu Ser Gln Ser His Arg Phe Lys Gly Pro Cys Val Ser
1               5                   10                  15

Lys Ser Asn Cys Ala Ala Val Cys Gln Thr Glu Gly Phe His Gly Gly
            20                  25                  30

His Cys Arg Gly Phe Arg Arg Arg Cys Phe Cys Thr Lys Arg Cys
        35                  40                  45
```

<210> SEQ ID NO 23
<211> LENGTH: 312
<212> TYPE: DNA
<213> ORGANISM: Artificial Sequence
<220> FEATURE:
<223> OTHER INFORMATION: coding sequence N. benthamiana pro-thionin - linker 1- D4E1

<400> SEQUENCE: 23

```
atggcaaact ccatgcgctt ctttgcaact gtgttactta tagcattgct tgtcacggct     60

accgagatgg gaccaatgac aattgcagag gcaagaactt gtgagtccca gagccaccgt    120

ttcaagggac catgctcaag agatagcaac tgtgccaccg tttgtctgac cgaaggattt    180

tccggtggcg actgccgtgg attccgccgc cgttgtttct gtaccaggcc ttgctcaggc    240

ggtgactgcc gaggaatgtt taagcttcgt gcaaaaatca aggtgaggtt gagagctaag    300

attaaactct ga                                                        312
```

<210> SEQ ID NO 24
<211> LENGTH: 102
<212> TYPE: PRT
<213> ORGANISM: Artificial Sequence
<220> FEATURE:
<223> OTHER INFORMATION: N. benthamiana pro-thionin - linker 1- D4E1

<400> SEQUENCE: 24

```
Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Arg
            20                  25                  30

Thr Cys Glu Ser Gln Ser His Arg Phe Lys Gly Pro Cys Ser Arg Asp
        35                  40                  45

Ser Asn Cys Ala Thr Val Cys Leu Thr Glu Gly Phe Ser Gly Gly Asp
    50                  55                  60

Cys Arg Gly Phe Arg Arg Arg Cys Phe Cys Thr Arg Pro Cys Gly Ser
65                  70                  75                  80

Thr Ala Pro Pro Ala Phe Lys Leu Arg Ala Lys Ile Lys Val Arg Leu
                85                  90                  95

Arg Ala Lys Ile Lys Leu
            100
```

<210> SEQ ID NO 25
<211> LENGTH: 220
<212> TYPE: DNA
<213> ORGANISM: Artificial Sequence
<220> FEATURE:
<223> OTHER INFORMATION: coding sequence N. benthamiana thionin - linker -continued

```
      1- D4E1

<400> SEQUENCE: 25

aagaacttgt gagtcccaga gccaccgttt caagggacca tgctcaagag atagcaactg     60

tgccaccgtt tgtctgaccg aaggattttc cggtggcgac tgccgtggat tccgccgccg    120

ttgtttctgt accaggcctt gctcaggcgg tgactgccga ggaatgttta agcttcgtgc    180

aaaaatcaag gtgaggttga gagctaagat taaactctga                          220


<210> SEQ ID NO 26
<211> LENGTH: 71
<212> TYPE: PRT
<213> ORGANISM: Artificial Sequence
<220> FEATURE:
<223> OTHER INFORMATION: N. benthamiana thionin - linker 1- D4E1

<400> SEQUENCE: 26

Arg Thr Cys Glu Ser Gln Ser His Arg Phe Lys Gly Pro Cys Ser Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Arg Cys Phe Cys Thr Arg Pro Cys Gly
        35                  40                  45

Ser Thr Ala Pro Pro Ala Phe Lys Leu Arg Ala Lys Ile Lys Val Arg
    50                  55                  60

Leu Arg Ala Lys Ile Lys Leu
65                  70


<210> SEQ ID NO 27
<211> LENGTH: 306
<212> TYPE: DNA
<213> ORGANISM: Artificial Sequence
<220> FEATURE:
<223> OTHER INFORMATION: coding sequence citrus pro-thionin - linker
      1- D4E1

<400> SEQUENCE: 27

atggagcgct cagtgcgttt attttcaact gttctacttg tgctgctgct tcttgccagt     60

gaaatggggc tgagggcggc agaagctagg atatgcgagt ctcagagtca ccggttcaag    120

gggccatgtg tgagtaagag caactgtgct gctgtttgcc aaactgaagg gttccacggt    180

ggccactgcc gtggattccg tcgtcgatgc ttttgcacta aaagatgttc aggcggtgac    240

tgccgaggaa tgtttaagct tcgtgcaaaa atcaaggtga ggttgagagc taagattaaa    300

ctctga                                                               306


<210> SEQ ID NO 28
<211> LENGTH: 100
<212> TYPE: PRT
<213> ORGANISM: Artificial Sequence
<220> FEATURE:
<223> OTHER INFORMATION: citrus pro-thionin - linker 1- D4E1

<400> SEQUENCE: 28

Met Glu Arg Ser Val Arg Leu Phe Ser Thr Val Leu Leu Val Leu Leu
1               5                   10                  15

Leu Leu Ala Ser Glu Met Gly Leu Arg Ala Ala Glu Ala Arg Ile Cys
            20                  25                  30

Glu Ser Gln Ser His Arg Phe Lys Gly Pro Cys Val Ser Lys Ser Asn
        35                  40                  45
```

-continued

```
Cys Ala Ala Val Cys Gln Thr Glu Gly Phe His Gly Gly His Cys Arg
    50                  55                  60

Gly Phe Arg Arg Arg Cys Phe Cys Thr Lys Arg Cys Gly Ser Thr Ala
65                  70                  75                  80

Pro Pro Ala Phe Lys Leu Arg Ala Lys Ile Lys Val Arg Leu Arg Ala
                85                  90                  95

Lys Ile Lys Leu
            100


<210> SEQ ID NO 29
<211> LENGTH: 219
<212> TYPE: DNA
<213> ORGANISM: Artificial Sequence
<220> FEATURE:
<223> OTHER INFORMATION: coding sequence citrus thionin - linker 1- D4E1

<400> SEQUENCE: 29

aggatatgcg agtctcagag tcaccggttc aaggggccat gtgtgagtaa gagcaactgt      60

gctgctgttt gccaaactga agggttccac ggtggccact gccgtggatt ccgtcgtcga     120

tgcttttgca ctaaaagatg ttcaggcggt gactgccgag gaatgtttaa gcttcgtgca     180

aaaatcaagg tgaggttgag agctaagatt aaactctga                            219


<210> SEQ ID NO 30
<211> LENGTH: 71
<212> TYPE: PRT
<213> ORGANISM: Artificial Sequence
<220> FEATURE:
<223> OTHER INFORMATION: citrus thionin - linker 1- D4E1

<400> SEQUENCE: 30

Arg Ile Cys Glu Ser Gln Ser His Arg Phe Lys Gly Pro Cys Val Ser
1               5                   10                  15

Lys Ser Asn Cys Ala Ala Val Cys Gln Thr Glu Gly Phe His Gly Gly
            20                  25                  30

His Cys Arg Gly Phe Arg Arg Arg Cys Phe Cys Thr Lys Arg Cys Gly
        35                  40                  45

Ser Thr Ala Pro Pro Ala Phe Lys Leu Arg Ala Lys Ile Lys Val Arg
    50                  55                  60

Leu Arg Ala Lys Ile Lys Leu
65                  70


<210> SEQ ID NO 31
<211> LENGTH: 223
<212> TYPE: DNA
<213> ORGANISM: Artificial Sequence
<220> FEATURE:
<223> OTHER INFORMATION: coding sequence D4E1 - linker 1- N. benthamiana
      thionin

<400> SEQUENCE: 31

atgtttaagc ttcgtgcaaa aatcaaggtg aggttgagag ctaagattaa actctgatca      60

ggcggtgact gccgaggaaa gaacttgtga gtcccagagc caccgtttca agggaccatg     120

ctcaagagat agcaactgtg ccaccgtttg tctgaccgaa ggattttccg gtggcgactg     180

ccgtggattc cgccgccgtt gtttctgtac caggccttgc taa                       223


<210> SEQ ID NO 32
<211> LENGTH: 71
<212> TYPE: PRT
<213> ORGANISM: Artificial Sequence
```

<220> FEATURE:
<223> OTHER INFORMATION: D4E1 - linker 1- N. benthamiana thionin

<400> SEQUENCE: 32

Phe Lys Leu Arg Ala Lys Ile Lys Val Arg Leu Arg Ala Lys Ile Lys
1 5 10 15

Leu Gly Ser Thr Ala Pro Pro Ala Arg Thr Cys Glu Ser Gln Ser His
20 25 30

Arg Phe Lys Gly Pro Cys Ser Arg Asp Ser Asn Cys Ala Thr Val Cys
35 40 45

Leu Thr Glu Gly Phe Ser Gly Gly Asp Cys Arg Gly Phe Arg Arg Arg
50 55 60

Cys Phe Cys Thr Arg Pro Cys
65 70

<210> SEQ ID NO 33
<211> LENGTH: 310
<212> TYPE: DNA
<213> ORGANISM: Artificial Sequence
<220> FEATURE:
<223> OTHER INFORMATION: coding sequence D4E1 - linker 1- optimized thionin

<400> SEQUENCE: 33
atgtttaagc ttcgtgcaaa aatcaaggtg aggttgagag ctaagattaa actctgatca 60
ggcggtgact gccgaggaca gaacttgtga gtctcaatct cataggttta aaggtccttg 120
tagtcgcgat tccaattgtg cgacagtatg tctcacggaa gggttttcag gcggtgactg 180
ccgaggattt cgccgtagat gcagatgcac tcggccatgt gttttcgatg aaaaaggaag 240
cactgctcca cctgcattca aactacgtgc taagattaag gtcagactga gagcgaagat 300
taagttgtga 310

<210> SEQ ID NO 34
<211> LENGTH: 76
<212> TYPE: PRT
<213> ORGANISM: Artificial Sequence
<220> FEATURE:
<223> OTHER INFORMATION: D4E1 - linker 1- optimized thionin

<400> SEQUENCE: 34

Phe Lys Leu Arg Ala Lys Ile Lys Val Arg Leu Arg Ala Lys Ile Lys
1 5 10 15

Leu Gly Ser Thr Ala Pro Pro Ala Arg Thr Cys Glu Ser Gln Ser His
20 25 30

Arg Phe Lys Gly Pro Cys Ser Arg Asp Ser Asn Cys Ala Thr Val Cys
35 40 45

Leu Thr Glu Gly Phe Ser Gly Gly Asp Cys Arg Gly Phe Arg Arg Arg
50 55 60

Cys Arg Cys Thr Arg Pro Cys Val Phe Asp Glu Lys
65 70 75

<210> SEQ ID NO 35
<211> LENGTH: 222
<212> TYPE: DNA
<213> ORGANISM: Artificial Sequence
<220> FEATURE:
<223> OTHER INFORMATION: coding sequence D4E1 - linker 1- citrus thionin

<400> SEQUENCE: 35
atgtttaagc ttcgtgcaaa aatcaaggtg aggttgagag ctaagattaa actctgatca 60
ggcggtgact gccgaggaag gatatgcgag tctcagagtc accggttcaa ggggccatgt 120
gtgagtaaga gcaactgtgc tgctgtttgc caaactgaag ggttccacgg tggccactgc 180
cgtggattcc gtcgtcgatg cttttgcact aaaagatgtt aa 222

<210> SEQ ID NO 36
<211> LENGTH: 71
<212> TYPE: PRT
<213> ORGANISM: Artificial Sequence
<220> FEATURE:
<223> OTHER INFORMATION: D4E1 - linker 1- citrus thionin

<400> SEQUENCE: 36

Phe Lys Leu Arg Ala Lys Ile Lys Val Arg Leu Arg Ala Lys Ile Lys
1 5 10 15

Leu Gly Ser Thr Ala Pro Pro Ala Arg Ile Cys Glu Ser Gln Ser His
20 25 30

Arg Phe Lys Gly Pro Cys Val Ser Lys Ser Asn Cys Ala Ala Val Cys
35 40 45

Gln Thr Glu Gly Phe His Gly Gly His Cys Arg Gly Phe Arg Arg Arg
50 55 60

Cys Phe Cys Thr Lys Arg Cys
65 70

<210> SEQ ID NO 37
<211> LENGTH: 87
<212> TYPE: DNA
<213> ORGANISM: Citrus sinensis

<400> SEQUENCE: 37
atggagcgct cagtgcgttt attttcaact gttctacttg tgctgctgct tcttgccagt 60
gaaatggggc tgagggcggc agaagct 87

<210> SEQ ID NO 38
<211> LENGTH: 29
<212> TYPE: PRT
<213> ORGANISM: Citrus sinensis

<400> SEQUENCE: 38

Met Glu Arg Ser Val Arg Leu Phe Ser Thr Val Leu Leu Val Leu Leu
1 5 10 15

Leu Leu Ala Ser Glu Met Gly Leu Arg Ala Ala Glu Ala
20 25

<210> SEQ ID NO 39
<211> LENGTH: 4
<212> TYPE: PRT
<213> ORGANISM: Artificial Sequence
<220> FEATURE:
<223> OTHER INFORMATION: linker 2

<400> SEQUENCE: 39

Gly Ser Thr Ala
1

<210> SEQ ID NO 40
<211> LENGTH: 13
<212> TYPE: PRT
<213> ORGANISM: Artificial Sequence
<220> FEATURE:
<223> OTHER INFORMATION: linker 3

<400> SEQUENCE: 40

Gly Gly Gly Gly Ser Gly Gly Gly Gly Thr Asp Gly Arg
1               5                   10

<210> SEQ ID NO 41
<211> LENGTH: 25
<212> TYPE: PRT
<213> ORGANISM: Artificial Sequence
<220> FEATURE:
<223> OTHER INFORMATION: linker 4

<400> SEQUENCE: 41

Lys Lys Pro Arg Phe Ile Thr Ala Ala Asp Phe Ser Ile Gly Ser Pro
1               5                   10                  15

Tyr Lys Pro Asn Asn Lys Val His Glu
            20                  25

<210> SEQ ID NO 42
<211> LENGTH: 44
<212> TYPE: PRT
<213> ORGANISM: Artificial Sequence
<220> FEATURE:
<223> OTHER INFORMATION: linker 5

<400> SEQUENCE: 42

Arg Lys Ile Thr Thr Ile Ala Thr Thr Ala Leu Leu Asp Asp Asn Asn
1               5                   10                  15

Asn Asn Pro Thr Thr Ser Asn Ser Thr Ser Gly Asn Val Val Asn Asn
            20                  25                  30

Ile Ser Ala Leu Asn Pro Ser Gly Arg Ser His Val
        35                  40

<210> SEQ ID NO 43
<211> LENGTH: 69
<212> TYPE: DNA
<213> ORGANISM: Artificial Sequence
<220> FEATURE:
<223> OTHER INFORMATION: ligation fragment

<400> SEQUENCE: 43
cccgggatgt ttaagcttcg tgcaaaaatc aaggtgaggt tgagagctaa gattaaactc     60
tgaggtacc                                                             69

<210> SEQ ID NO 44
<211> LENGTH: 264
<212> TYPE: DNA
<213> ORGANISM: Artificial Sequence
<220> FEATURE:
<223> OTHER INFORMATION: ligation fragment

<400> SEQUENCE: 44
cccgggatgg caaactcgat gaggttcttt gctacagttt tattgatcgc acttcttgtg     60
accgctacag agatgggtcc gatgaccata gctgaagcca gaacttgtga gtctcaatct    120
cataggttta aaggtccttg tagtcgcgat tccaattgtg cgacagtatg tctcacggaa    180
gggttttcag gcggtgactg ccgaggattt cgccgtagat gcagatgcac tcggccatgt    240
gttttcgatg aaaaatgagg tacc                                           264

<210> SEQ ID NO 45
<211> LENGTH: 342
<212> TYPE: DNA
<213> ORGANISM: Artificial Sequence
<220> FEATURE:
<223> OTHER INFORMATION: ligation fragment

<400> SEQUENCE: 45
cccggggaaa caatggcaaa ctcgatgagg ttctttgcta cagttttatt gatcgcactt 60
cttgtgaccg ctacagagat gggtccgatg accatagctg aagccagaac ttgtgagtct 120
caatctcata ggtttaaagg tccttgtagt cgcgattcca attgtgcgac agtatgtctc 180
acggaagggt tttcaggcgg tgactgccga ggatttcgcc gtagatgcag atgcactcgg 240
ccatgtgttt tcgatgaaaa aggaagcact gctccacctg cattcaaact acgtgctaag 300
attaaggtca gactgagagc gaagattaag ttgtgaggta cc 342

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
gacgcacaat cccactatcc 20

<210> SEQ ID NO 47
<211> LENGTH: 21
<212> TYPE: DNA
<213> ORGANISM: Artificial Sequence
<220> FEATURE:
<223> OTHER INFORMATION: primer

<400> SEQUENCE: 47
tttgcgcgct atattttgtt t 21

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
caaggtgagg ttgagagcta ag 22

<210> SEQ ID NO 49
<211> LENGTH: 22
<212> TYPE: DNA
<213> ORGANISM: Artificial Sequence
<220> FEATURE:
<223> OTHER INFORMATION: primer

<400> SEQUENCE: 49
tcctagtttg cgcgctatat tt 22

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
tttcgccgta gatgcagatg 20

<210> SEQ ID NO 51

-continued

<211> LENGTH: 22
<212> TYPE: DNA
<213> ORGANISM: Artificial Sequence
<220> FEATURE:
<223> OTHER INFORMATION: primer

<400> SEQUENCE: 51
tcctagtttg cgcgctatat tt 22

<210> SEQ ID NO 52
<211> LENGTH: 23
<212> TYPE: DNA
<213> ORGANISM: Nicotiana benthamiana

<400> SEQUENCE: 52
gaccactgaa gttggatctg ttg 23

<210> SEQ ID NO 53
<211> LENGTH: 22
<212> TYPE: DNA
<213> ORGANISM: Nicotiana benthamiana

<400> SEQUENCE: 53
tagcaccagt tgggtccttc tt 22

<210> SEQ ID NO 54
<211> LENGTH: 11
<212> TYPE: PRT
<213> ORGANISM: Artificial Sequence
<220> FEATURE:
<223> OTHER INFORMATION: linker 6

<400> SEQUENCE: 54

Gly Ser Arg Ala Pro Pro Ala Gly Ser Thr Ala
1 5 10

<210> SEQ ID NO 55
<211> LENGTH: 315
<212> TYPE: DNA
<213> ORGANISM: Artificial Sequence
<220> FEATURE:
<223> OTHER INFORMATION: coding sequence pro-D4E1-Linker 1- N. benthamiana thionin

<400> SEQUENCE: 55
atggcaaact cgatgaggtt ctttgctaca gttttattga tcgcacttct tgtgaccgct 60
acagagatgg gtccgatgac catagctgaa gcatgtttaa gcttcgtgca aaaatcaagg 120
tgaggttgag agctaagatt aaactctgat caggcggtga ctgccgagga aagaacttgt 180
gagtcccaga gccaccgttt caagggacca tgctcaagag atagcaactg tgccaccgtt 240
tgtctgaccg aaggatttc cggtggcgac tgccgtggat tccgccgccg ttgtttctgt 300
accaggcctt gctaa 315

<210> SEQ ID NO 56
<211> LENGTH: 102
<212> TYPE: PRT
<213> ORGANISM: Artificial Sequence
<220> FEATURE:
<223> OTHER INFORMATION: pro-D4E1 - linker 1- N. benthamiana thionin

<400> SEQUENCE: 56

Met Ala Asn Ser Met Arg Phe Phe Ala Thr Val Leu Leu Ile Ala Leu
1 5 10 15

-continued

```
Leu Val Thr Ala Thr Glu Met Gly Pro Met Thr Ile Ala Glu Ala Phe
            20                  25                  30

Lys Leu Arg Ala Lys Ile Lys Val Arg Leu Arg Ala Lys Ile Lys Leu
        35                  40                  45

Gly Ser Thr Ala Pro Pro Ala Arg Thr Cys Glu Ser Gln Ser His Arg
    50                  55                  60

Phe Lys Gly Pro Cys Ser Arg Asp Ser Asn Cys Ala Thr Val Cys Leu
65                  70                  75                  80

Thr Glu Gly Phe Ser Gly Gly Asp Cys Arg Gly Phe Arg Arg Arg Cys
                85                  90                  95

Phe Cys Thr Arg Pro Cys
            100


<210> SEQ ID NO 57
<211> LENGTH: 402
<212> TYPE: DNA
<213> ORGANISM: Artificial Sequence
<220> FEATURE:
<223> OTHER INFORMATION: coding sequence pro-D4E1 - linker 1- optimized
      thionin

<400> SEQUENCE: 57

atggcaaact cgatgaggtt ctttgctaca gttttattga tcgcacttct tgtgaccgct     60

acagagatgg gtccgatgac catagctgaa gcatgtttaa gcttcgtgca aaaatcaagg    120

tgaggttgag agctaagatt aaactctgat caggcggtga ctgccgagga cagaacttgt    180

gagtctcaat ctcataggtt taaaggtcct tgtagtcgcg attccaattg tgcgacagta    240

tgtctcacgg aagggttttc aggcggtgac tgccgaggat ttcgccgtag atgcagatgc    300

actcggccat gtgttttcga tgaaaaagga agcactgctc cacctgcatt caaactacgt    360

gctaagatta aggtcagact gagagcgaag attaagttgt ga                       402


<210> SEQ ID NO 58
<211> LENGTH: 107
<212> TYPE: PRT
<213> ORGANISM: Artificial Sequence
<220> FEATURE:
<223> OTHER INFORMATION: pro-D4E1 - linker 1- optimized thionin

<400> SEQUENCE: 58

Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Phe
            20                  25                  30

Lys Leu Arg Ala Lys Ile Lys Val Arg Leu Arg Ala Lys Ile Lys Leu
        35                  40                  45

Gly Ser Thr Ala Pro Pro Ala Arg Thr Cys Glu Ser Gln Ser His Arg
    50                  55                  60

Phe Lys Gly Pro Cys Ser Arg Asp Ser Asn Cys Ala Thr Val Cys Leu
65                  70                  75                  80

Thr Glu Gly Phe Ser Gly Gly Asp Cys Arg Gly Phe Arg Arg Arg Cys
                85                  90                  95

Arg Cys Thr Arg Pro Cys Val Phe Asp Glu Lys
            100                 105


<210> SEQ ID NO 59
<211> LENGTH: 314
<212> TYPE: DNA
<213> ORGANISM: Artificial Sequence
```

-continued

<220> FEATURE:
<223> OTHER INFORMATION: coding sequence pro-D4E1 - linker 1- citrus thionin

<400> SEQUENCE: 59

```
atggcaaact cgatgaggtt ctttgctaca gttttattga tcgcacttct tgtgaccgct     60

acagagatgg gtccgatgac catagctgaa gcatgtttaa gcttcgtgca aaaatcaagg    120

tgaggttgag agctaagatt aaactctgat caggcggtga ctgccgagga aggatatgcg    180

agtctcagag tcaccggttc aaggggccat gtgtgagtaa gagcaactgt gctgctgttt    240

gccaaactga agggttccac ggtggccact gccgtggatt ccgtcgtcga tgcttttgca    300

ctaaaagatg ttaa                                                      314
```

<210> SEQ ID NO 60
<211> LENGTH: 102
<212> TYPE: PRT
<213> ORGANISM: Artificial Sequence
<220> FEATURE:
<223> OTHER INFORMATION: pro-D4E1 - linker 1- citrus thionin

<400> SEQUENCE: 60

```
Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Phe
            20                  25                  30

Lys Leu Arg Ala Lys Ile Lys Val Arg Leu Arg Ala Lys Ile Lys Leu
        35                  40                  45

Gly Ser Thr Ala Pro Pro Ala Arg Ile Cys Glu Ser Gln Ser His Arg
    50                  55                  60

Phe Lys Gly Pro Cys Val Ser Lys Ser Asn Cys Ala Ala Val Cys Gln
65                  70                  75                  80

Thr Glu Gly Phe His Gly Gly His Cys Arg Gly Phe Arg Arg Arg Cys
                85                  90                  95

Phe Cys Thr Lys Arg Cys
            100
```

<210> SEQ ID NO 61
<211> LENGTH: 149
<212> TYPE: DNA
<213> ORGANISM: Artificial Sequence
<220> FEATURE:
<223> OTHER INFORMATION: coding sequence pro-D4E1

<400> SEQUENCE: 61

```
atggcaaact cgatgaggtt ctttgctaca gttttattga tcgcacttct tgtgaccgct     60

acagagatgg gtccgatgac catagctgaa gcatgtttaa gcttcgtgca aaaatcaagg    120

tgaggttgag agctaagatt aaactctga                                      149
```

<210> SEQ ID NO 62
<211> LENGTH: 48
<212> TYPE: PRT
<213> ORGANISM: Artificial Sequence
<220> FEATURE:
<223> OTHER INFORMATION: pro-D4E1

<400> SEQUENCE: 62

```
Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Phe
```

-continued

```
            20                  25                  30

Lys Leu Arg Ala Lys Ile Lys Val Arg Leu Arg Ala Lys Ile Lys Leu
        35                  40                  45


<210> SEQ ID NO 63
<211> LENGTH: 25
<212> TYPE: DNA
<213> ORGANISM: Candidatus Liberibacter asiaticus

<400> SEQUENCE: 63

cttaccagcc cttgacatgt atagg                                           25


<210> SEQ ID NO 64
<211> LENGTH: 30
<212> TYPE: DNA
<213> ORGANISM: Candidatus Liberibacter asiaticus

<400> SEQUENCE: 64

tccctataaa gtacccaaca tctaggtaaa                                      30


<210> SEQ ID NO 65
<211> LENGTH: 20
<212> TYPE: DNA
<213> ORGANISM: Citrus sinensis

<400> SEQUENCE: 65

tgagtacgag ccgagtgttg                                                 20


<210> SEQ ID NO 66
<211> LENGTH: 21
<212> TYPE: DNA
<213> ORGANISM: Citrus sinensis

<400> SEQUENCE: 66

aaaacttcac cgatccacca g                                               21


<210> SEQ ID NO 67
<211> LENGTH: 104
<212> TYPE: PRT
<213> ORGANISM: Artificial Sequence
<220> FEATURE:
<223> OTHER INFORMATION: Optimized pro-thionin - linker 2 - D4E1

<400> SEQUENCE: 67

Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Arg
            20                  25                  30

Thr Cys Glu Ser Gln Ser His Arg Phe Lys Gly Pro Cys Ser Arg Asp
        35                  40                  45

Ser Asn Cys Ala Thr Val Cys Leu Thr Glu Gly Phe Ser Gly Gly Asp
    50                  55                  60

Cys Arg Gly Phe Arg Arg Arg Cys Arg Cys Thr Arg Pro Cys Val Phe
65                  70                  75                  80

Asp Glu Lys Gly Ser Thr Ala Phe Lys Leu Arg Ala Lys Ile Lys Val
                85                  90                  95

Arg Leu Arg Ala Lys Ile Lys Leu
            100


<210> SEQ ID NO 68
<211> LENGTH: 113
```

<212> TYPE: PRT
<213> ORGANISM: Artificial Sequence
<220> FEATURE:
<223> OTHER INFORMATION: Optimized pro-thionin - linker 3 - D4E1

<400> SEQUENCE: 68

```
Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Arg
            20                  25                  30

Thr Cys Glu Ser Gln Ser His Arg Phe Lys Gly Pro Cys Ser Arg Asp
        35                  40                  45

Ser Asn Cys Ala Thr Val Cys Leu Thr Glu Gly Phe Ser Gly Gly Asp
    50                  55                  60

Cys Arg Gly Phe Arg Arg Arg Cys Arg Cys Thr Arg Pro Cys Val Phe
65                  70                  75                  80

Asp Glu Lys Gly Gly Gly Gly Ser Gly Gly Gly Gly Thr Asp Gly Arg
                85                  90                  95

Phe Lys Leu Arg Ala Lys Ile Lys Val Arg Leu Arg Ala Lys Ile Lys
            100                 105                 110

Leu
```

<210> SEQ ID NO 69
<211> LENGTH: 125
<212> TYPE: PRT
<213> ORGANISM: Artificial Sequence
<220> FEATURE:
<223> OTHER INFORMATION: Optimized pro-thionin - linker 4 - D4E1

<400> SEQUENCE: 69

```
Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Arg
            20                  25                  30

Thr Cys Glu Ser Gln Ser His Arg Phe Lys Gly Pro Cys Ser Arg Asp
        35                  40                  45

Ser Asn Cys Ala Thr Val Cys Leu Thr Glu Gly Phe Ser Gly Gly Asp
    50                  55                  60

Cys Arg Gly Phe Arg Arg Arg Cys Arg Cys Thr Arg Pro Cys Val Phe
65                  70                  75                  80

Asp Glu Lys Lys Lys Pro Arg Phe Ile Thr Ala Ala Asp Phe Ser Ile
                85                  90                  95

Gly Ser Pro Tyr Lys Pro Asn Asn Lys Val His Glu Phe Lys Leu Arg
            100                 105                 110

Ala Lys Ile Lys Val Arg Leu Arg Ala Lys Ile Lys Leu
        115                 120                 125
```

<210> SEQ ID NO 70
<211> LENGTH: 144
<212> TYPE: PRT
<213> ORGANISM: Artificial Sequence
<220> FEATURE:
<223> OTHER INFORMATION: Optimized pro-thionin - linker 5 - D4E1

<400> SEQUENCE: 70

```
Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Arg
            20                  25                  30
```

```
Thr Cys Glu Ser Gln Ser His Arg Phe Lys Gly Pro Cys Ser Arg Asp
        35                  40                  45

Ser Asn Cys Ala Thr Val Cys Leu Thr Glu Gly Phe Ser Gly Gly Asp
    50                  55                  60

Cys Arg Gly Phe Arg Arg Arg Cys Arg Cys Thr Arg Pro Cys Val Phe
65                  70                  75                  80

Asp Glu Lys Arg Lys Ile Thr Thr Ile Ala Thr Thr Ala Leu Leu Asp
                85                  90                  95

Asp Asn Asn Asn Asn Pro Thr Thr Ser Asn Ser Thr Ser Gly Asn Val
            100                 105                 110

Val Asn Asn Ile Ser Ala Leu Asn Pro Ser Gly Arg Ser His Val Phe
        115                 120                 125

Lys Leu Arg Ala Lys Ile Lys Val Arg Leu Arg Ala Lys Ile Lys Leu
    130                 135                 140


<210> SEQ ID NO 71
<211> LENGTH: 73
<212> TYPE: PRT
<213> ORGANISM: Artificial Sequence
<220> FEATURE:
<223> OTHER INFORMATION: Optimized thionin - linker 2 - D4E1

<400> SEQUENCE: 71

Arg Thr Cys Glu Ser Gln Ser His Arg Phe Lys Gly Pro Cys Ser Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Arg Cys Arg Cys Thr Arg Pro Cys Val
        35                  40                  45

Phe Asp Glu Lys Gly Ser Thr Ala Phe Lys Leu Arg Ala Lys Ile Lys
    50                  55                  60

Val Arg Leu Arg Ala Lys Ile Lys Leu
65                  70


<210> SEQ ID NO 72
<211> LENGTH: 82
<212> TYPE: PRT
<213> ORGANISM: Artificial Sequence
<220> FEATURE:
<223> OTHER INFORMATION: Optimized thionin - linker 3 - D4E1

<400> SEQUENCE: 72

Arg Thr Cys Glu Ser Gln Ser His Arg Phe Lys Gly Pro Cys Ser Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Arg Cys Arg Cys Thr Arg Pro Cys Val
        35                  40                  45

Phe Asp Glu Lys Gly Gly Gly Gly Ser Gly Gly Gly Gly Thr Asp Gly
    50                  55                  60

Arg Phe Lys Leu Arg Ala Lys Ile Lys Val Arg Leu Arg Ala Lys Ile
65                  70                  75                  80

Lys Leu


<210> SEQ ID NO 73
<211> LENGTH: 94
<212> TYPE: PRT
<213> ORGANISM: Artificial Sequence
```

```
<220> FEATURE:
<223> OTHER INFORMATION: Optimized thionin - linker 4 - D4E1

<400> SEQUENCE: 73

Arg Thr Cys Glu Ser Gln Ser His Arg Phe Lys Gly Pro Cys Ser Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Arg Cys Arg Cys Thr Arg Pro Cys Val
        35                  40                  45

Phe Asp Glu Lys Lys Lys Pro Arg Phe Ile Thr Ala Ala Asp Phe Ser
    50                  55                  60

Ile Gly Ser Pro Tyr Lys Pro Asn Asn Lys Val His Glu Phe Lys Leu
65                  70                  75                  80

Arg Ala Lys Ile Lys Val Arg Leu Arg Ala Lys Ile Lys Leu
                85                  90


<210> SEQ ID NO 74
<211> LENGTH: 113
<212> TYPE: PRT
<213> ORGANISM: Artificial Sequence
<220> FEATURE:
<223> OTHER INFORMATION: Optimized thionin - linker 5 - D4E1

<400> SEQUENCE: 74

Arg Thr Cys Glu Ser Gln Ser His Arg Phe Lys Gly Pro Cys Ser Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Arg Cys Arg Cys Thr Arg Pro Cys Val
        35                  40                  45

Phe Asp Glu Lys Arg Lys Ile Thr Thr Ile Ala Thr Thr Ala Leu Leu
    50                  55                  60

Asp Asp Asn Asn Asn Asn Pro Thr Thr Ser Asn Ser Thr Ser Gly Asn
65                  70                  75                  80

Val Val Asn Asn Ile Ser Ala Leu Asn Pro Ser Gly Arg Ser His Val
                85                  90                  95

Phe Lys Leu Arg Ala Lys Ile Lys Val Arg Leu Arg Ala Lys Ile Lys
            100                 105                 110

Leu


<210> SEQ ID NO 75
<211> LENGTH: 73
<212> TYPE: PRT
<213> ORGANISM: Artificial Sequence
<220> FEATURE:
<223> OTHER INFORMATION: D4E1 - linker 2 - Optimized thionin

<400> SEQUENCE: 75

Phe Lys Leu Arg Ala Lys Ile Lys Val Arg Leu Arg Ala Lys Ile Lys
1               5                   10                  15

Leu Gly Ser Thr Ala Arg Thr Cys Glu Ser Gln Ser His Arg Phe Lys
            20                  25                  30

Gly Pro Cys Ser Arg Asp Ser Asn Cys Ala Thr Val Cys Leu Thr Glu
        35                  40                  45

Gly Phe Ser Gly Gly Asp Cys Arg Gly Phe Arg Arg Arg Cys Arg Cys
    50                  55                  60

Thr Arg Pro Cys Val Phe Asp Glu Lys
```

65 70

<210> SEQ ID NO 76
<211> LENGTH: 80
<212> TYPE: PRT
<213> ORGANISM: Artificial Sequence
<220> FEATURE:
<223> OTHER INFORMATION: D4E1 - linker 6 - Optimized thionin

<400> SEQUENCE: 76

```
Phe Lys Leu Arg Ala Lys Ile Lys Val Arg Leu Arg Ala Lys Ile Lys
1               5                   10                  15

Leu Gly Ser Arg Ala Pro Pro Ala Gly Ser Thr Ala Arg Thr Cys Glu
            20                  25                  30

Ser Gln Ser His Arg Phe Lys Gly Pro Cys Ser Arg Asp Ser Asn Cys
        35                  40                  45

Ala Thr Val Cys Leu Thr Glu Gly Phe Ser Gly Gly Asp Cys Arg Gly
    50                  55                  60

Phe Arg Arg Arg Cys Arg Cys Thr Arg Pro Cys Val Phe Asp Glu Lys
65                  70                  75                  80
```

<210> SEQ ID NO 77
<211> LENGTH: 104
<212> TYPE: PRT
<213> ORGANISM: Artificial Sequence
<220> FEATURE:
<223> OTHER INFORMATION: pro-D4E1 - linker 2 - Optimized thionin

<400> SEQUENCE: 77

```
Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Phe
            20                  25                  30

Lys Leu Arg Ala Lys Ile Lys Val Arg Leu Arg Ala Lys Ile Lys Leu
        35                  40                  45

Gly Ser Thr Ala Arg Thr Cys Glu Ser Gln Ser His Arg Phe Lys Gly
    50                  55                  60

Pro Cys Ser Arg Asp Ser Asn Cys Ala Thr Val Cys Leu Thr Glu Gly
65                  70                  75                  80

Phe Ser Gly Gly Asp Cys Arg Gly Phe Arg Arg Arg Cys Arg Cys Thr
                85                  90                  95

Arg Pro Cys Val Phe Asp Glu Lys
            100
```

<210> SEQ ID NO 78
<211> LENGTH: 107
<212> TYPE: PRT
<213> ORGANISM: Artificial Sequence
<220> FEATURE:
<223> OTHER INFORMATION: pro-D4E1 - linker 6 - Optimized thionin

<400> SEQUENCE: 78

```
Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Phe
            20                  25                  30

Lys Leu Arg Ala Lys Ile Lys Val Arg Leu Arg Ala Lys Ile Lys Leu
        35                  40                  45

Gly Ser Thr Ala Pro Pro Ala Arg Thr Cys Glu Ser Gln Ser His Arg
    50                  55                  60
```

-continued

```
Phe Lys Gly Pro Cys Ser Arg Asp Ser Asn Cys Ala Thr Val Cys Leu
65                  70                  75                  80

Thr Glu Gly Phe Ser Gly Gly Asp Cys Arg Gly Phe Arg Arg Arg Cys
                85                  90                  95

Arg Cys Thr Arg Pro Cys Val Phe Asp Glu Lys
            100                 105
```

THIONIN-D4E1 CHIMERIC PROTEIN PROTECTS PLANTS AGAINST BACTERIAL INFECTIONS

STATEMENT REGARDING FEDERALLY SPONSORED RESEARCH OR DEVELOPMENT

The United States government has rights in this invention pursuant to Contract No. DE-AC52-06NA25396 between the United States Department of Energy and Los Alamos National Security, LLC for the operation of Los Alamos National Laboratory.

BACKGROUND OF THE INVENTION

Field of the Invention

This invention relates to a chimeric protein made from a combination of thionin and D4E1. This invention also relates to genetically altered plants that can express this chimeric protein, and the use of the chimeric protein to protect plants against bacterial infections.

Description of Related Art

Plants have developed multiple defense mechanisms to combat invading pathogenic microorganisms. For example, plants will synthesize antimicrobial compound such as antimicrobial peptides (AMPs), thionins and defensins. See, Broekaert, et al., *Critical Review in Plant Sci.* 16:297-323 (2007). Many AMPs have been identified from various organisms. AMPs are short peptides with broad spectrum antimicrobial activity against bacteria and fungi. AMPs can damage a pathogen's cell membrane by inhibiting chitin synthase or β-D-glucan synthase. See, DeLucca and Walsh, *Antimicrobial Agent and Chemotherapy* 43:1-11 (1999). D4E1, one such antimicrobial peptide which is also a synthetic peptide, has a β-sheet conformation in solution and during interaction with cell membranes which results in lytic activity. See, DeLucca, et al., *Can. J. Microbiol.* 44:514-520 (1998). In order to optimize the activity against target pathogens, chimeric protein constructions, with or without modification of amino acid sequences, have been designed including the anti-fungal and anti-bacterial lactoferricin B derivatives (Marcos, et al., *Annu. Rev. Phytopathol.* 46:273-301 (2008), antifungal cecropin A and cecropin A-mellitin derived peptides (Monroc, et al., *Peptides* 27:2567-2574 (2006); Monroc, et al., *Peptides* 27:2575-2584 (2006); and Cavallarín, et al., *Mol. Plant Microbe Interact.* 11:218-227 (1998)), and bactericidal cyclic decapeptide BPC194 series (Monroc, et al., *Peptides* 27:2567-2574 (2006); and Monroc, et al., *Peptides* 27:2575-2584 (2006)), and antifungal hexapeptide PAF26 (López-García, et al., *Mol. Plant Microbe Interact.* 13:837-846 (2000); and López-García, et al., *Appl. Environ. Microbiol.* 68:2453-2460 (2002).

Many studies have reported that the expression of naturally occurring peptides and their analogs confer resistance to pathogens in transgenic plants including *Arabidopsis* (Lee, et al., *Plant Physiol.* 148:1004-1020 (2008)), tobacco (Huang, et al., *Phytopathology* 87:494-499 (1997); Jaynes, et al., *Plant Sci.* 89:43-53 (1993); and Cary, et al., *Plant Sci.* 154:171-181 (2000)), Chinese cabbage (Jung, et al., *Plant Biotechnol. Rep.* 6:39-46 (2012)), rice (Coca, et al., *Planta* 223:392-406 (2006), and Imamura, et al. *Transgenic Res.* 19:415-424 (2010)), cotton (Rajasekaran, et al., *Plant Biotechnol. J.* 3:545-554 (2006)), tomato (Alan, et al., *Plant Cell Rep.* 22:388-396 (2006), and Alan, et al., *Plant Cell Rep.* 22:388-396 (2006)), potato (Osusky, et al., *Transgenic Res.* 13:181-190 (2004)), pear (Reynoird, et al., *Plant Sci.* 149:23-31 (1999)), banana (Chakrabarti, et al., *Planta* 216: 587-596 (2003)), and hybrid poplar (Mentag, et al., *Tree Physiol.* 23:405-411 (2003)).

Compared to naturally produced peptides, synthetic peptides such as D4E1 show rapid biocontrol or biostatic ability against various fungal and bacterial pathogens at low concentrations and can be designed to be non-toxic to mammalian and other animal cells (Jaynes, et al., *Peptide Res.* 2:157-160 (1989). In addition, synthetic peptides are generally designed to resist degradation by fungal and plant proteases and show target specificity and increased efficacy (Broekaert, et al. (2007), and Montesinos, E, *FEMS Microbio. Lett.* 270:1-11 (2007)). Haemolytic activity of synthetic peptide D4E1 was found to be very low (Jaynes, et al., *Plant Sci.* 89:43-54 (1993)). It has been demonstrated that the pure synthetic peptide D4E1 is inhibitory to growth of about 20 bacterial and fungal phytopathogens (Rajasekaran, et al., *J. Agric. Food Chem.* 49:2799-2803 (2001)). In addition, transgenic tobacco plants expressing D4E1 demonstrated a significant reduction in fungal growth in vitro and in planta (Cary, et al., *Plant Sci.* 154:171-181 (2000)). A 50% to 90% reduction in the viability of *Fusarium verticillioides* and *Verticillium dahliae* was reported when spores were incubated in crude protein extracts of D4E1-transformed cotton compared to extracts from GUS-transformed cotton (Rajasekaran, et al., *Plant Biotechnol. J.* 3:545-554 (2005)). D4E1 is effective in killing *Chlamydia trachomatis* in-vitro (Ballweber, et al., *Antimicrobial Agents and Chemotherapy* 46:1, 34-41 (2002)). Purified D4E1 is highly effective at killing *Agrobacterium tumefaciens, Sinorhizobium meliloti*, and *Xanthomonas citri* ssp. *citri*, but shows little hemolysis of porcine erythrocytes (Stover, et al., *J. Amer. Soc. Hort. Sci.* 138:142-148 (2013)).

Thionins from barley leaf are toxic to phytopathogenic bacteria and fungi in-vitro (Bohlmann, et al., *EMBO J.* 7:1559-1566 (1988); Molina, et al., *Plant Sci.* 92:169-177 (1993)). Thionins are small basic peptides containing between approximately 44 and approximately 47 amino acids and contain a conserved cysteine-rich domain with toxic and antimicrobial properties. Thionins are classified into two groups, a/b-thionins and c-thionins, based on their 3-D structure (Pelegrini and Franco, *Int. J. Biochem. Cell. Bio.* 37:2239-2253 (2005)). Thionins are postulated to induce the opening of pores on the pathogen-cell membranes, allowing escape of potassium and calcium ions from pathogens' cell(s) (Pelegrini and Franco (2005); Oard, S. V., *Biochim. Biophys. Acta* 1808:1737-1745 (2011)). It has been showed that a thionin gene from barley seed increased resistance to *Pseudomonas syringae* when overproduced in transgenic tobacco plants (Carmona, et al., *Plant J.* 3:457-462 (1993)). Overexpression of the *Arabidopsis* thionin thi2.1 gene in *Arabidopsis* plants resulted in enhanced resistance to *Fusarium oxysporum* (Epple, et al., *Plant Cell* 9:509-520 (1997). Transgenic rice plants overproducing oat thionin displayed enhanced resistance to the bacterial diseases caused by *Burkholderia plantarii* and *B. glumae* (Iwai, et al., *Mol. Plant Microbe Interact.* 15:837-846 (2002)). Likewise, transgenic sweet potato overproducing barley α-hordothionin had increased resistance to black rot disease caused by *Ceratocystis fimbriata* (Muramoto, et al., *Plant Cell Rep.* 31:987-97 (2012)).

To improve the efficacy of these anti-microbial agents, plants transformed to express chimeric proteins containing two different proteins or peptides have been assessed. In a recent study, grape plants were transformed to express a chimeric protein containing human neutrophil elastase and cecropin B. These transgenic grape plants had resistance against *Xylella fastidiosa* ssp. *fastidiosa* which causes Pierce disease in grapevines. See, Dandekar, et al., *Proc. Nat. Acad. Sci.* 109:10 3721-3725 (2012). These finding are important because *X. fastidiosa* is a Gram-negative bacterial pathogen with a wide range of plant hosts of economic importance.

Huanglongbing (HLB) (also called "citrus greening") and citrus canker cause serious diseases that threaten the Florida citrus industry. The causative agents of HLB are *Candidatus Liberibacter africanus* (CLaf), *Candidatus Liberibacter asiaticus* (CLas), and *Candidatus Liberibacter americanus* (CLam). The bacteria are transmitted from plant to plant via Asian citrus psyllid (*Diaphorina citri*), the African citrus psyllid (*Trioza erytreae*), and, perhaps, other hemipteran insects that feed from citrus plants' vascular tissue. Citrus canker is caused by *Xanthomonas citri* ssp. *citri* (Xcc). Xcc are spread by wind and perhaps insects and enter into citrus plants via wounds or other openings in the bark. These diseases are devastating the citrus industry in Florida because of no effective treatment currently exists. Furthermore, both diseases and the causative pathogens are spreading to other parts of the U.S. and other citrus-producing countries.

A need exists for a method to prevent and/or treat these diseases in citrus plants. A need also exists to prevent and/or treat bacterial diseases in plants. This invention involves genetically altered citrus plants that can produce a chimeric protein having broad-spectrum antimicrobial activity against gram-negative bacteria which can confer resistance to both citrus greening and canker diseases in citrus plants. This invention also involves other genetically altered plants expressing this chimeric protein and that have resistance to diseases caused by bacteria.

BRIEF DESCRIPTION OF THE INVENTION

It is an object of this invention to have a chimeric protein that has a first domain, a second domain, and a third domain. It is another object of this invention that the first domain is a thionin or pro-thionin, the second domain is D4E1 or pro-D4E1, and the third domain is a peptide linker which separates the first domain from the second domain such that the first domain and the second domain can each fold into its appropriate three-dimensional shape and retains its bacterial activity. It is another object of this invention that the peptide linker ranges in length between approximately three amino acids and approximately forty-four amino acids. It is another object of this invention that the first domain and the second domain are positioned within this chimeric protein such that either the first domain or the second domain is at the amino terminus of the chimeric protein with the other domain (second domain or first domain, respectively) is located at the carboxyl terminus of the chimeric protein. It is another object of this invention that this chimeric protein, when expressed in genetically altered plants, kills bacteria and protects the genetically altered plant from diseases caused by bacteria.

It is another object of this invention that, when the first domain of this chimeric protein is located at the amino terminal of the chimeric protein, the first domain can be a thionin or pro-thionin from a plant (such as, but not limited to a citrus plant or *Nicotiana benthamiana*) or can be an artificial thionin or pro-thionin which has been optimized (optimized thionin or optimized pro-thionin). It is another object of this invention that, when the first domain is located at the amino terminal of the chimeric protein, the second domain is located at the carboxyl terminal of the chimeric protein and is D4E1. It is another object of this invention that the third domain is a peptide linker which separates the first domain from the second domain such that the first domain and the second domain can each fold into its appropriate three-dimensional shape and retains its bacterial activity. It is another object of this invention that the first domain has the amino acid sequence of SEQ ID NO: 4, SEQ ID NO: 6, SEQ ID NO: 14, SEQ ID NO: 16, SEQ ID NO: 20, or SEQ ID NO: 22. It is a further object of this invention that the second domain has the amino acid sequence of SEQ ID NO: 2. It is yet another object of this invention that the peptide linker has the amino acid sequence of SEQ ID NO: 10, SEQ ID NO: 39, SEQ ID NO: 40, SEQ ID NO: 41, or SEQ ID NO: 42. It is another object of this invention that this chimeric protein, when expressed in genetically altered plants, kills bacteria and protects the genetically altered plant from diseases caused by bacteria.

It is an object of this invention that, when the first domain of this chimeric protein is located at the carboxyl terminus of the chimeric protein, the first domain is a thionin from a plant (such as, but not limited to a citrus plant or *Nicotiana benthamiana*) or can be an artificial thionin which has been optimized (optimized thionin). It is another object of this invention that, when the first domain is located at the carboxyl terminal of the chimeric protein, the second domain is located at the amino terminus of the chimeric protein and is either D4E1 or pro-D4E1. It is another object of this invention that the third domain is a peptide linker which separates the first domain from the second domain such that the first domain and the second domain can each fold into its appropriate three-dimensional shape and retains its bacterial activity. It is another object of this invention that the thionin (first domain) has the amino acid of SEQ ID NO: 14, SEQ ID NO: 20, or SEQ ID NO: 22. It is a further object of this invention that the second domain, D4E1 or pro-D4E1, has the amino acid sequence of SEQ ID NO: 2 or SEQ ID NO: 62. It is another object of this invention that the peptide linker has the amino acid sequence of SEQ ID NO: 10, SEQ ID NO: 39, or SEQ ID NO: 54. It is another object of this invention that this chimeric protein, when expressed in genetically altered plants, kills bacteria and protects the genetically altered plant from diseases caused by bacteria.

It is an object of this invention to have a chimeric protein that has a first domain at the amino terminus of the chimeric protein, a second domain at the carboxyl terminus of the chimeric protein, and a third domain that is a peptide linker that separates the first domain and the second domain such that the first domain and the second domain can each fold into its appropriate three-dimensional shape and retains its bacterial activity. It is another object of this invention that the first domain is a thionin or pro-thionin, and the second domain is D4E1. It is another object of this invention that the chimeric protein has the amino acid sequence of SEQ ID NO: 8, SEQ ID NO: 18, SEQ ID NO: 24, SEQ ID NO: 26, SEQ ID NO: 28, SEQ ID NO: 30, SEQ ID NO: 67, SEQ ID NO: 68, SEQ ID NO: 69, SEQ ID NO: 70, SEQ ID NO: 71, SEQ ID NO: 72, SEQ ID NO: 73, or SEQ ID NO: 74. It is another object of this invention that this chimeric protein, when expressed in genetically altered plants, kills bacteria and protects the genetically altered plant from diseases caused by bacteria.

It is an object of this invention to have a chimeric protein that has a first domain at the carboxyl terminus of the chimeric protein, a second domain at the amino terminus of the chimeric protein, and a third domain that is a peptide linker that separates the first domain and the second domain such that the first domain and the second domain can each fold into its appropriate three-dimensional shape and retains its bacterial activity. It is another object of this invention that the first domain is a thionin, and the second domain is D4E1 or pro-D4E1. It is another object of this invention that the chimeric protein has an amino acid sequence of SEQ ID NO: 32, SEQ ID NO: 34, SEQ ID NO: 36, SEQ ID NO: 56, SEQ ID NO: 58, SEQ ID NO: 60, SEQ ID NO: 75, SEQ ID NO: 76, SEQ ID NO: 77, or SEQ ID NO: 78.

It is a further object of this invention to have one or more polynucleotides that encodes the chimeric proteins of this invention. It is yet another object of this invention to have an expression vector that contains a promoter operably linked to one or more polynucleotides that encodes the chimeric proteins. It is a further object of this invention to have a genetically altered plant or part thereof and its progeny that contains one or more of the polynucleotides of this invention. It is an object of this invention to have a flower, seed, or pollen of this genetically altered plant. It is yet another object of this invention to have a genetically altered plant cell or tissue culture of genetically altered plant cells that contain one or more polynucleotides encoding the chimeric proteins of this invention operably linked to a promoter.

It is an object of this invention to have a method of constructing a genetically altered plant or part thereof having increased resistance to bacterial infections compared to a non-genetically altered plant or part thereof. It is a further object of this invention that the method involves introducing one or more polynucleotides encoding one or more of the chimeric proteins of this invention into a plant or part thereof to provide or generate a genetically altered plant or part thereof and selecting a genetically altered plant or part thereof that expresses the chimeric protein and that the expressed chimeric protein has anti-bacterial activity. This chimeric protein has a first domain, a second domain, and a third domain such that the first domain can be thionin or pro-thionin, the second domain can be D4E1 or pro-D4E1, and the third domain is a peptide linker that separates the first domain from the second domain such that the first domain and the second domain can each fold into its appropriate three-dimensional shape and retains its bacterial activity, and such that the peptide linker ranges in length between approximately three amino acids and approximately forty-four amino acids. It is a further object of the invention that introducing the one or more polynucleotides encoding the one or more chimeric proteins of this invention occurs via introgression or transforming the plant with an expression vector containing the one or more polynucleotides operably linked to a promoter. It is an optional object of this invention that, when the first domain is located at the amino terminus of the chimeric protein, it has the amino acid sequence of SEQ ID NO: 4, SEQ ID NO: 6, SEQ ID NO: 14, SEQ ID NO: 16, SEQ ID NO: 20, or SEQ ID NO: 22; and that, when the second domain is located at the carboxyl terminus of the chimeric protein, it has the amino acid sequence of SEQ ID NO: 2; and that the peptide linker has the amino acid sequence of SEQ ID NO: 10, SEQ ID NO: 39, SEQ ID NO: 40, SEQ ID NO: 41, or SEQ ID NO: 42. It is another optional object of this invention that, when the second domain is located at the amino terminus of the chimeric protein, it has the amino acid sequence of SEQ ID NO: 2 or SEQ ID NO: 62; and that, when the first domain is located at the carboxyl terminus of the chimeric protein, it has an amino acid sequence of SEQ ID NO: 14, SEQ ID NO: 20, or SEQ ID NO: 22; and that the peptide linker has the amino acid sequence of SEQ ID NO: 10, SEQ ID NO: 39, or SEQ ID NO: 54. It is another object of this invention that the polynucleotide encodes a chimeric protein that has the amino acid sequence of SEQ ID NO: 8, SEQ ID NO: 18, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 56, SEQ ID NO: 58, SEQ ID NO: 60, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, or SEQ ID NO: 78. It is an optional object of this invention that the polynucleotide has the DNA sequence of SEQ ID NO: 7, SEQ ID NO: 17, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 55, SEQ ID NO: 57, SEQ ID NO: 59, or SEQ ID NO: 61.

It is another object of this invention to have a method of enhancing a plant's resistance to bacterial diseases by transforming the plant or part thereof with one or more polynucleotides that encode one or more of chimeric proteins of this invention to generate a genetically altered plant or part there of such that the genetically altered plant or part thereof produces the chimeric protein which kills bacteria that cause bacterial diseases. This chimeric protein has a first domain, a second domain, and a third domain, such that the first domain can be thionin or pro-thionin, the second domain can be D4E1 or pro-D4E1, and the third domain is a peptide linker that separates the first domain from the second domain such that the first domain and the second domain can each fold into its appropriate three-dimensional shape and retains its bacterial activity, and such that the peptide linker ranges in length between approximately three amino acids and approximately forty-four amino acids. It is an optional object of this invention that, when the first domain is located at the amino terminus of the chimeric protein, it has the amino acid sequence of SEQ ID NO: 4, SEQ ID NO: 6, SEQ ID NO: 14, SEQ ID NO: 16, SEQ ID NO: 20, or SEQ ID NO: 22; and that, when the second domain is located at the carboxyl terminus of the chimeric protein, it has the amino acid sequence of SEQ ID NO: 2; and that the peptide linker has the amino acid sequence of SEQ ID NO: 10, SEQ ID NO: 39, SEQ ID NO: 40, SEQ ID NO: 41, or SEQ ID NO: 42. It is another optional object of this invention that, when the second domain is located at the amino terminus of the chimeric protein, it has the amino acid sequence of SEQ ID NO: 2 or SEQ ID NO: 62; and that, when the first domain is located at the carboxyl terminus of the chimeric protein, it has an amino acid sequence of SEQ ID NO: 14, SEQ ID NO: 20, or SEQ ID NO: 22; and that the peptide linker has the amino acid sequence of SEQ ID NO: 10, SEQ ID NO: 39, or SEQ ID NO: 54. Optionally, the polynucleotide encodes a chimeric protein that has the amino acid sequence of SEQ ID NO: 8, SEQ ID NO: 18, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 56, SEQ ID NO: 58, SEQ ID NO: 60, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, or SEQ ID NO: 78. It is an optional object of this invention that the polynucleotide has the DNA sequence of SEQ ID NO: 7, SEQ ID NO: 17, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 55, SEQ ID NO: 57, SEQ ID NO: 59, or SEQ ID NO: 61.

BRIEF DESCRIPTION OF THE DRAWINGS

FIG. 1 compares the amino acid sequences of *Nicotiana benthamiana* pro-thionin (SEQ ID NO: 4), citrus pro-thionin (SEQ ID NO: 16), and optimized pro-thionin (SEQ ID NO: 6).

FIG. 2 shows diagrams for the three binary vector pBIN-PLUS/ARS containing the desired polynucleotides encoding the heterologous proteins (D4E1, "thionin" is optimized pro-thionin, and "chimera" is optimized pro-thionin-linker 1-D4E1). In FIG. 2, "LB" is left border; "Ubi3-p" is the Ubi3 promoter; "NPTII" is neomycin phosphotransferase gene (which confers kanamycin resistance); "Ubi3-t" is Ubi3 terminator; "D35S-p" is double CaMV 35S promoter; "Nos-t" is nos terminator; and "RB" is right border. Thin arrows indicate position of PCR primers to confirm gene integration located between D35S promoter and nos terminator regions. Thick arrow heads indicate locations of primers for RT-PCR and RT-qPCR located in target genes and nos terminator regions.

FIG. 3A shows the 300 bp RT-PCR fragment for the chimeric protein. FIG. 3B shows the 500 bp RT-PCR fragment for *N. benthamiana* EF1α (NbEF1α). FIG. 3C shows the 220 bp RT-PCR fragment for the optimized pro-thionin protein. FIG. 3D shows the 500 bp RT-PCR fragment for NbEF1α. FIG. 3E shows the 220 bp RT-PCR fragment for the D4E1 protein. FIG. 3F shows the 500 bp RT-PCR fragment for NbEF1α.

DETAILED DESCRIPTION OF THE INVENTION

Figure 3A:
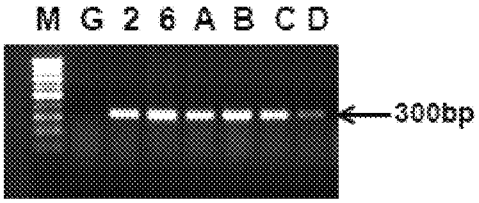
FIG. 3A and FIG. 3B show two gels loaded with the RT-PCR amplification of total RNA from six genetically altered *N. benthamiana* plants (lanes 2, 6, A, B, C, and D) expressing the heterologous chimeric protein (optimized pro-thionin-linker 1-D4E1), molecular weight marker (lane M), and genetically altered *N. benthamiana* plant expressing GUS (lane G).

In order to protect citrus plants from two devastating diseases, this invention involves the generation of a chimeric protein and genetically altered citrus plants to express the chimeric protein. This chimeric protein has the ability to protect citrus plants from *Xanthomonas citri* (the causative agent of canker) and from the *Candidatus Liberibacter* species (the causative agent of HBL or citrus greening disease). Genetically altered plants expressing/producing this chimeric protein exhibit no symptoms or much reduced symptoms of the diseases caused by these bacteria when exposed to the bacteria. It is also within the scope of this invention that any plant can be genetically altered to express the chimeric proteins described herein, and that the genetically altered plant will be protected from gram-negative bacterial infections because the expressed chimeric proteins kill the gram-negative bacteria that infect the plant. It is also within the scope of this invention that the chimeric proteins kill gram-positive bacteria.

Thus, this invention also covers the method of preventing or treating gram-negative or gram-positive bacterial diseases in a plant with altered DNA (and the plant's progeny) by transforming the plant (or otherwise altering the DNA of plant) with one or more polynucleotides which encode one or more of the chimeric proteins described herein and allow the plant to produce the one or more chimeric proteins. The chimeric protein will kill gram-negative bacteria after the gram-negative bacteria infect the plant. The invention also includes a method of enhancing a plant's resistance to bacterial diseases by transforming a plant (or otherwise altering the DNA of plant) with one or more polynucleotides encoding one or more chimeric proteins described herein such that the plant containing the heterologous DNA produces the chimeric protein, and the chimeric protein kills bacteria that cause bacterial diseases after the bacteria infect the plant.

In one embodiment of this invention, the chimeric protein has three domains, a first domain containing thionin or pro-thinion, a second domain containing D4E1, and a third domain containing a peptide linker. This peptide linker domain is a set of amino acids that separate the first domain from the second domain and prevents steric inhibition between the first domain and the second domain. In one embodiment, the first domain (thionin or pro-thinion) is at the amino terminus of the chimeric protein, and the second domain (D4E1) is at the carboxyl terminus. In another embodiment, the second domain (D4E1 or pro-D4E1) is at the amino terminus of the chimeric protein while the first domain (thionin) is at the carboxyl terminus.

When thionin is located at the amino terminus of the chimeric protein, it is encoded as a pro-protein (pro-thionin) which contains an amino acid signal sequence (the exact number of amino acids in the signal sequence can vary by organism). The signal sequence assists in the trafficking of pro-thionin to the endoplasmic reticulum or a cellular vesicle. Not wishing to be bound to a particular hypothesis, it is believed that the signal sequence is cleaved off pro-thionin prior to, during, or after passage of pro-thionin through the lipid membrane to yield mature thionin. See, Romero, et al., *Eur. J. Biochem.* 243:202-8 (1997). When thionin (first domain) is located at the carboxyl terminus of the chimeric protein, thionin (first domain) does not contain an amino acid signal sequence. However, the chimeric protein still can contain an amino acid signal sequence at the amino terminus of the chimeric protein as described below. The thionin (or pro-thionin) can be a thionin (or pro-thionin) that exists in a plant (and more specifically in *N. benthamiana* or a citrus plant), or an optimized thionin (or optimized pro-thionin) as described below. The third domain, the peptide linker, can be Linker 1 (SEQ ID NO: 10), Linker 2 (SEQ ID NO: 39), Linker 3 (SEQ ID NO: 40), Linker 4 (SEQ ID NO: 41), or Linker 5 (SEQ ID NO: 42).

When the second domain is located at the amino terminus of the chimeric protein and first domain is located at the carboxyl terminus, a signal sequence upstream of D4E1 can be used to traffic the chimeric protein to the endoplasmic reticulum or cellular vesicle. This signal sequence can be the signal sequence for the optimized pro-thionin or citrus' pro-thionin or any other signal sequence from a plant. Optimized pro-thionin's signal sequence is 31 amino acids long (SEQ ID NO: 12) and has the DNA sequence of SEQ ID NO: 11. The DNA sequence and amino acid sequence for citrus' pro-thionin signal sequence is in SEQ ID NO: 37 and SEQ ID NO: 38, respectively. Thus, when the second domain is located at the amino terminus of the chimeric protein, it can be D4E1 or pro-D4E1. The chimeric protein containing D4E1 or pro-D4E1 at the amino terminal can contain, in the third domain, Linker 1 (SEQ ID NO: 10), Linker 2 (SEQ ID NO: 39), or Linker 6 (SEQ ID NO: 54). Further, the first domain, located at the carboxyl terminus of the chimeric protein can be thionin (from *N. benthamiana* (SEQ ID NO: 19) or a citrus plant (SEQ ID NO: 22)) or optimized thionin (SEQ ID NO: 14). To be clear, the DNA sequence encoding the chimeric protein containing D4E1 or pro-D4E1 at the amino terminus does not encode pro-thionin (or optimized pro-thionin). Instead, the DNA sequence encodes mature thionin (or mature optimized thionin) (i.e., without the amino acid signal sequence). For the purposes of this invention, when a signal sequence is adjacent to D4E1, it is referred to as "pro-D4E1" because the signal sequence amino acids are removed during post-translational processing to generate the mature D4E1.

In one embodiment, the first domain of the chimeric protein contains "optimized thionin" (or optimized pro-thionin). The nucleotide and amino acid sequence of the optimized thionin differs from thionin naturally present in plants. One difference between optimized thionin and thionin from some plants is the addition of five amino acids at the carboxyl terminus of the protein. Optimized thionin also includes some amino acid substitutions, the number and location depending on the plant thionin sequence to which it is being compared. One substitution involves replacing an arginine to a phenylalanine. Optimized thionin has (i) an increase in anti-bacterial activity and (ii) a reduced toxicity to the plant compared to wild-type thionin (or "non-optimized" thionin). See FIG. 1 for a comparison of the amino acid sequences of *N. benthamiana* pro-thionin, citrus pro-thionin (obtained from *Citrus sinensis*), and optimized pro-thionin. The first 31 amino acids for *N. benthamiana* pro-thionin and optimized pro-thionin and the first 29 amino acids for citrus pro-thionin are the signal sequence amino acids for the respective proteins. In another embodiment, the first domain of the chimeric protein is citrus thionin (or citrus pro-thionin). In yet another embodiment, the first domain of the chimeric protein is *N. benthamiana* thionin (or *N. benthamiana* pro-thionin).

The third domain (peptide linker) can range from two amino acids long to approximately 50 amino acids long in one embodiment. In another embodiment, the linker domain ranges from three amino acids to approximately 44 amino acids. In another embodiment, the linker domain ranges from four amino acids to approximately 44 amino acids. In yet another embodiment, the linker domain is four, five, six, seven, eight, nine, ten, eleven, twelve, or thirteen amino acids long. A linker should be sufficiently flexible such that the first domain and the second domain of the chimeric protein are able to fold into their correct three-dimensional shape and retain their activity. The linker should not reduce solubility of the chimeric protein, and can, in certain circumstances, enhance solubility of the chimeric protein. The linker and the chimeric protein containing the particular linker should be non-toxic to the genetically altered plant expressing the chimeric protein. In one embodiment, the linker can assist in generating a synergistic effect between the first domain and second domain of the chimeric protein. Non-limiting examples of linkers are provided in Table 1, infra. As demonstrated in the examples, below, genetically altered plants expressing the chimeric protein have better/greater antibacterial activity than genetically altered plants expressing either optimized thionin (or thionin) only or D4E1 only. This greater antibacterial activity is surprising and unexpected. It is believed that this better/greater anti-bacterial activity results from the synergistic effect of having D4E1 and optimized thionin (or thionin) attached via a peptide linker (and thus exist as "one" protein).

This invention covers the various chimeric proteins having the different configurations disclosed herein, their amino acid sequences, and their DNA sequences. This invention also covers genetically altered plants which carry heterologous DNA encoding one or more of the chimeric proteins described herein and which can express the one or more chimeric proteins encoded by the heterologous DNA. As such, expression vectors which contain heterologous DNA (encoding a chimeric protein) operably linked to a promoter are also covered in this invention. To help in the generations of the expression vectors and genetically altered plants containing the heterologous DNA encoding a chimeric protein, the DNA sequences encoding the chimeric proteins disclosed herein may include additional nucleotides at the 5' and 3' end of the polynucleotide which assist in generating the expression vectors and/or assist in the transcription of the polynucleotide into mRNA and/or translation of the mRNA into the chimeric protein.

In the examples below, plants are genetically altered to express either D4E1, optimized thionin (or optimized pro-thionin), or one of the chimeric proteins discussed herein. This invention also covers plants which contain these heterologous DNA via introgression. To assist in understanding the examples and inventions described herein, Table 1 lists the various proteins or polypeptides and their DNA and/or amino acid sequence listing number. One can use the information in Table 1 to generate a chimeric protein containing linker 2, linker 3, linker 4, linker 5, or linker 6 with the desired thionin instead of optimized thionin and with D4E1.

TABLE 1

| Protein or polypeptide | DNA sequence # | Amino acid sequence # |
|---|---|---|
| D4E1 | SEQ ID NO: 1 | SEQ ID NO: 2 |
| Pro-D4E1 | SEQ ID NO: 61 | SEQ ID NO: 62 |
| *N. benthamiana* pro-thionin | SEQ ID NO: 3 | SEQ ID NO: 4 |
| *N. benthamiana* thionin | SEQ ID NO: 19 | SEQ ID NO: 20 |
| Citrus pro-thionin (*Citrus sinensis*) | SEQ ID NO: 15 | SEQ ID NO: 16 |
| Citrus thionin (*Citrus sinensis*) | SEQ ID NO: 21 | SEQ ID NO: 22 |
| Optimized pro-thionin | SEQ ID NO: 5 | SEQ ID NO: 6 |
| Optimized thionin | SEQ ID NO: 13 | SEQ ID NO: 14 |
| Chimeric protein (*N. benthamiana* pro-thionin - linker 1 - D4E1) | SEQ ID NO: 23 | SEQ ID NO: 24 |
| Chimeric protein (*N. benthamiana* thionin - linker 1 - D4E1) | SEQ ID NO: 25 | SEQ ID NO: 26 |
| Chimeric protein (optimized pro-thionin - linker 1 - D4E1) | SEQ ID NO: 7 | SEQ ID NO: 8 |
| Chimeric protein (optimized thionin - linker 1 - D4E1) | SEQ ID NO: 17 | SEQ ID NO: 18 |
| Chimeric protein (citrus pro-thionin - linker 1 - D4E1) | SEQ ID NO: 27 | SEQ ID NO: 28 |

TABLE 1-continued

| Protein or polypeptide | DNA sequence # | Amino acid sequence # |
|---|---|---|
| Chimeric protein (citrus thionin - linker 1 - D4E1) | SEQ ID NO: 29 | SEQ ID NO: 30 |
| Chimeric protein (optimized pro-thionin - linker 2 - D4E1) | | SEQ ID NO: 67 |
| Chimeric protein (optimized pro-thionin - linker 3 - D4E1) | | SEQ ID NO: 68 |
| Chimeric protein (optimized pro-thionin - linker 4 - D4E1) | | SEQ ID NO: 69 |
| Chimeric protein (optimized pro-thionin - linker 5 - D4E1) | | SEQ ID NO: 70 |
| Chimeric protein (optimized thionin - linker 2 - D4E1) | | SEQ ID NO: 71 |
| Chimeric protein (optimized thionin - linker 3 - D4E1) | | SEQ ID NO: 72 |
| Chimeric protein (optimized thionin - linker 4 - D4E1) | | SEQ ID NO: 73 |
| Chimeric protein (optimized thionin - linker 5 - D4E1) | | SEQ ID NO: 74 |
| Chimeric protein (D4E1 - linker 1 - *N. benthamiana* thionin) | SEQ ID NO: 31 | SEQ ID NO: 32 |
| Chimeric protein (D4E1 - linker 1 - optimized thionin) | SEQ ID NO: 33 | SEQ ID NO: 34 |
| Chimeric protein (D4E1 - linker 1 - citrus thionin) | SEQ ID NO: 35 | SEQ ID NO: 36 |
| Chimeric protein (pro-D4E1 - linker 1 - *N. benthamiana* thionin) | SEQ ID NO: 55 | SEQ ID NO: 56 |
| Chimeric protein (pro-D4E1 - linker 1 - optimized thionin) | SEQ ID NO: 57 | SEQ ID NO: 58 |
| Chimeric protein (pro-D4E1 - linker 1 - citrus thionin) | SEQ ID NO: 59 | SEQ ID NO: 60 |
| Chimeric protein (D4E1 - linker 2 - optimized thionin) | | SEQ ID NO: 75 |
| Chimeric protein (D4E1 - linker 6 - optimized thionin) | | SEQ ID NO: 76 |
| Chimeric protein (pro-D4E1 - linker 2 - optimized thionin) | | SEQ ID NO: 77 |
| Chimeric protein (pro-D4E1 - linker 6 - optimized thionin) | | SEQ ID NO: 78 |
| Signal sequence for optimized pro-thionin and *N. benthamiana* pro-thionin | SEQ ID NO: 11 | SEQ ID NO: 12 |
| Signal sequence for citrus pro-thionin | SEQ ID NO: 37 | SEQ ID NO: 38 |
| Linker 1 | SEQ ID NO: 9 | SEQ ID NO: 10 |
| Linker 2 | | SEQ ID NO: 39 |
| Linker 3 | | SEQ ID NO: 40 |
| Linker 4 | | SEQ ID NO: 41 |
| Linker 5 | | SEQ ID NO: 42 |
| Linker 6 | | SEQ ID NO: 54 |

The chimeric peptides of this invention are effective against a wide range of gram-negative plant-pathogenic bacteria. Examples of diseases caused by gram-negative bacteria include, but not be limited, to crown gall (caused by *Agrobacterium* spp.); Pierce's Disease, Almond Scorch, Coffee Scorch, and Citrus Variegated Chlorosis (caused by *Xylella* spp.); citrus canker and various bacterial blights, spots and wilts (caused by *Xanthomonas* spp.); blasts, leaf spots, cankers and diebacks (caused by *Pseudomonas* spp.); and blights and soft-rots (caused by *Erwinia* spp.). In addition to CLas, CLam, and CLaf that cause HLB disease in citrus plants, other *Candidatus Liberibacter* species infect various plants and are pathogenic. For example, *Candidatus Liberibacter psyllaurous* infects potato and tomato plants, and *Candidatus Liberibacter solanacearum* infect potato plants causing zebra chip disease. Other bacteria that infect plants and cause disease are known in the art. Genetically altered plants expressing the chimeric protein(s) describe herein have enhanced protection against these diseases and the pathogens causing the diseases.

Because this invention involves production of genetically altered plants and involves recombinant DNA techniques, the following definitions are provided to assist in describing this invention. The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). Because the amino acid sequences of D4E1, thionin, pro-thionin, optimized thionin, optimized pro-thionin, linker 1, linker 2, linker 3, linker 4, linker 5, linker 6, and the chimeric proteins are described, one can chemically synthesize a polynucleotide which encodes these polypeptides/chimeric proteins. Because of the degeneracy of nucleic acid codons, one can use various different polynucleotides to encode identical polypeptides. Table 2, infra, contains information about which nucleic acid codons encode which amino acids.

TABLE 2

| Amino acid | Nucleic acid codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. "Conservative amino acid substitutions" are those substitutions that are predicted to interfere least with the properties of the reference polypeptide. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide. Table 3 provides a list of exemplary conservative amino acid substitutions. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

TABLE 3

| Amino Acid | Conservative Substitute |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Ile, Leu |
| Phe | His, Leu, Met, Trp, Tyr |
| Ser | Cys, Thr |
| Thr | Ser, Val |
| Trp | Phe, Tyr |
| Tyr | His, Phe, Trp |
| Val | Ile, Leu, Thr |

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed—over-expressed, under-expressed or not expressed at all.

The terms "transgenic", "transformed", "transformation", and "transfection" are similar in meaning to "recombinant". "Transformation", "transgenic", and "transfection" refer to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

A genetically altered organism is any organism with any change to its genetic material, whether in the nucleus or cytoplasm (organelle). As such, a genetically altered organism can be a recombinant or transformed organism. A genetically altered organism can also be an organism that was subjected to one or more mutagens or the progeny of an organism that was subjected to one or more mutagens and has changes in its DNA caused by the one or more mutagens, as compared to the wild-type organism (i.e, organism not subjected to the mutagens). Also, an organism that has been bred to incorporate a mutation into its genetic material is a genetically altered organism. For the purposes of this invention, the organism is a plant.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature; etc. There are various types of vectors including virus, plasmid, bacteriophages, cosmids, and bacteria.

An expression vector is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" is a polynucleotide containing a section of an expression vector of this invention. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is operably linked to an expression control sequence(s) (e.g., a promoter and, optionally, an enhancer) when the expression control sequence controls and regulates the transcription and/or translation of that polynucleotide sequence.

Transformation and generation of genetically altered monocotyledonous and dicotyledonous plant cells is well known in the art. See, e.g., Weising, et al., *Ann. Rev. Genet.* 22:421-477 (1988); U.S. Pat. No. 5,679,558; *Agrobacterium Protocols*, ed: Gartland, Humana Press Inc. (1995); and Wang, et al. *Acta Hort.* 461:401-408 (1998). The choice of method varies with the type of plant to be transformed, the particular application and/or the desired result. The appropriate transformation technique is readily chosen by the skilled practitioner.

Exemplary transformation/transfection methods available to those skilled in the art include, but are not limited to: direct uptake of foreign DNA constructs (see, e.g., EP 295959); techniques of electroporation (see, e.g., Fromm et al., *Nature* 319:791 (1986)); and high-velocity ballistic bombardment with metal particles coated with the nucleic acid constructs (see, e.g., Kline, et al., *Nature* 327:70 (1987) and U.S. Pat. No. 4,945,050). Specific methods to transform heterologous genes into commercially important crops (to make genetically altered plants) are published for rapeseed (De Block, et al., *Plant Physiol.* 91:694-701 (1989)); sunflower (Everett, et al., *Bio/Technology* 5:1201 (1987)); soybean (McCabe, et al., *Bio/Technology* 6:923 (1988), Hinchee, et al., *Bio/Technology* 6:915 (1988), Chee, et al., *Plant Physiol.* 91:1212-1218 (1989), and Christou, et al., *Proc. Natl. Acad. Sci USA* 86:7500-7504 (1989)); rice (Hiei, et al., *Plant J.* 6:271-282 (1994)), and corn (Gordon-Kamm, et al., *Plant Cell* 2:603-618 (1990), and Fromm, et al., *Biotechnology* 8:833-839 (1990)). Other known methods are disclosed in U.S. Pat. Nos. 5,597,945; 5,589,615; 5,750,871; 5,268,526; 5,262,316; and 5,569,831.

One exemplary method includes employing *Agrobacterium tumefaciens* or *Agrobacterium rhizogenes* as the transforming agent to transfer heterologous DNA into the plant. *Agrobacterium tumefaciens*-meditated transformation techniques are well described in the scientific literature. See, e.g., Horsch, et al. *Science* 233:496-498 (1984), and Fraley, et al. *Proc. Natl. Acad. Sci. USA* 80:4803 (1983). Typically, a plant cell, an explant, a meristem or a seed is infected with *Agrobacterium tumefaciens* transformed with the expression vector/construct which contains the heterologous nucleic acid operably linked to a promoter. Under appropriate conditions known in the art, the transformed plant cells are grown to form shoots, roots, and develop further into genetically altered plants. In some embodiments, the heterologous nucleic acid can be introduced into plant cells, by means of the Ti plasmid of *Agrobacterium tumefaciens*. The Ti plasmid is transmitted to plant cells upon infection by *Agrobacterium tumefaciens*, and is stably integrated into the plant genome. See, e.g., Horsch, et al. (1984), and Fraley, et al. (1983).

Transformed plant cells which are derived by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture*, in *Handbook of Plant Cell Culture*, pp. 124-176, MacMillan Publishing Company, New York, 1983; and Binding, *Regeneration of Plants*, in *Plant Protoplasts*, pp. 21-73, CRC Press, Boca Raton, 1985. Regeneration can also be obtained from plant callus, explants, organs, or parts thereof. Such regeneration techniques are described generally in Klee, et al., *Ann. Rev. of Plant Phys.* 38:467-486 (1987).

This invention utilizes routine techniques in the field of molecular biology. Basic texts disclosing the general methods of use in this invention include Green and Sambrook, 4th ed. 2012, Cold Spring Harbor Laboratory; Kriegler,

*Gene Transfer and Expression: A Laboratory Manual* (1993); and Ausubel et al., eds., *Current Protocols in Molecular Biology,* 1994—current, John Wiley & Sons. Unless otherwise noted, technical terms are used according to conventional usage. Definitions of common terms in molecular biology maybe found in e.g., Benjamin Lewin, *Genes IX*, published by Oxford University Press, 2007 (ISBN 0763740632); Krebs, et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The class of plants that can be used in the method of the invention is generally as broad as the class of higher and lower plants amenable to the molecular biology and plant breeding techniques described herein, specifically angiosperms (monocotyledonous (monocots) and dicotyledonous (dicots) plants). It includes plants of a variety of ploidy levels, including aneuploid, polyploid, diploid, haploid and hemizygous. The genetically altered plants described herein can be monocot crops, such as, sorghum, maize, wheat, rice, barley, oats, rye, millet, and triticale. The genetically altered plants described herein can also be dicot crops, such as apple, pear, peach, plum, orange, lemon, lime, grapefruit, pomegranate, olive, peanut, tobacco, etc. Also, the genetically altered plants (or plants with altered genomic DNA) can be horticultural plants such as rose, marigold, primrose, dogwood, pansy, geranium, etc. In some embodiments, the genetically altered plants are citrus plants. In other embodiments, the genetically altered plants are *N. benthamiana* or tobacco plants.

Once a genetically altered plant has been generated, one can breed it with a wild-type plant and screen for heterozygous F1 generation plants containing the genetic change present in the parent genetically altered plant. Then F2 generation plants can be generated which are homozygous for the genetic alteration. These heterozygous F1 generation plants and homozygous F2 plants, progeny of the original genetically altered plant, are considered genetically altered plants, having the altered genomic material from the genetically altered parent plant.

After one obtains a genetically altered plant expressing the chimeric protein, one can efficiently breed the genetically altered plant with other plants containing desired traits. One can use molecular markers (i.e., polynucleotide probes) based on the sequence of the chimeric protein as described above to determine which offspring of crosses between the genetically altered plant and the other plant have the polynucleotide encoding the chimeric protein. This process is known as Marker Assisted Rapid Trait Introgression (MARTI). Briefly, MARTI involves (1) crossing the genetically altered plant with a plant line having desired phenotype/genotype ("elite parent") for introgression to obtain F1 offspring. The F1 generation is heterozygous for chimeric protein trait. (2) Next, an F1 plant is be backcrossed to the elite parent, producing BC1F1 which genetically produces 50% wild-type and 50% heterozygote chimeric protein. (3) PCR using the polynucleotide probe is performed to select the heterozygote genetically altered plants containing polynucleotide encoding the chimeric protein. (4) Selected heterozygotes are then backcrossed to the elite parent to perform further introgression. (5) This process of MARTI is performed for another four cycles. (6) Next, the heterozygote genetically altered plant is self-pollinated by bagging to produce BC6F2 generation. The BC6F2 generation produces a phenotypic segregation ratio of 3 wild-type parent plants to 1 chimeric protein genetically altered plant. (7) One selects genetically altered chimeric protein plants at the BC6F2 generation at the seedling stage using PCR with the polynucleotide probe and can optionally be combined with phenotypic selection at maturity. These cycles of crossing and selection can be achieved in a span of 2 to 2.5 years (depending on the plant), as compared to many more years for conventional backcrossing introgression method now in use. Thus, the application of MARTI using PCR with a polynucleotide probe significantly reduces the time to introgress the chimeric protein genetic alteration into elite lines for producing commercial hybrids. The final product is an inbred plant line almost identical (99%) to the original elite in-bred parent plant that is the homozygous for the polynucleotide encoding the chimeric protein.

The terms "approximately" and "about" refer to a quantity, level, value or amount that varies by as much as 30%, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

Having described the invention in general terms, below are examples illustrating the generation and efficacy of the invention.

Example 1 Generation of Genetically Altered *N. benthamiana*

Genetically altered *N. benthamiana* plants are generated to assess the antibacterial efficacy of D4E1 (SEQ ID NO: 2), optimized thionin (SEQ ID NO: 14) or the chimeric protein, optimized thionin-linker 1-D4E1 (SEQ ID NO: 18). To improve the antibacterial activity of *N. benthamiana* thionin and to reduce its toxicity to *N. benthamiana* plants, in-silico assays are performed which indicate that thionin's activity could be enhanced by changing the DNA sequence so that optimized thionin contains five additional acidic amino acids compared to the wild-type *N. benthamiana* thionin amino acid sequence. In addition, an arginine is substituted for phenylalanine to reduce plant toxicity in optimized thionin. See FIG. 1 for a comparison of *N. benthamiana* pro-thionin amino acid sequence (SEQ ID NO: 4) and optimized pro-thionin amino acid sequence (SEQ ID NO: 6). The chimeric protein, optimized thionin-linker 1-D4E1 (SEQ ID NO: 18), contains linker 1 which is seven amino acids (peptide linker, third domain) (SEQ ID NO: 10) between the thionin domain (first domain) and the D4E1 domain (second domain) to reduce steric hindrance of the two active domains of the chimeric protein and so that each domain retains its antibacterial activity, thus generating a synergistic antibacterial activity. As discussed above, optimized thionin and the chimeric protein, optimized thionin-linker 1-D4E1, are encoded and translated as pro-thionin and contain 31 amino acids (SEQ ID NO: 12) as a signal sequence which assists in trafficking the pro-protein to and through the endoplasmic reticulum or a vesicle. The signal sequence amino acids are cleaved off the pro-peptide to generate the mature protein. The DNA and amino acid sequences for optimized pro-thionin are in SEQ ID NO: 5 and SEQ ID NO: 6, respectively; and the DNA and amino acid sequences for the chimeric protein, optimized pro-thionin-linker 1-D4E1 are in SEQ ID NO: 7 and SEQ ID NO: 8, respectively.

DNA2.0 (Menlo Park, Calif.) is hired to synthesize the DNA sequences for the three proteins (D4E1 only, optimized pro-thionin, and optimized pro-thionin-linker 1-D4E1 (chimeric protein or chimera)) which are used to generate the genetically altered *N. benthamiana* plants. To assist in the generation of the appropriate plasmids and expression vectors, each DNA sequence contains additional nucleotides at the 5' end and 3' end to generate recognition sites for restriction endonucleases Sma1 and Kpn1, respectively. Thus the DNA sequence of Sma1-D4E1-Kpn1 is in SEQ ID NO: 43. The DNA sequence of Sma1-optimized pro-thionin-Kpn1 is in SEQ ID NO: 44. The DNA sequence of Sma1-optimized pro-thionin-linker 1-D4E1-Kpn1 is in SEQ ID NO: 45. DNA 2.0 supplies the chemically synthesized polynucletoides in individual pJ224 plasmids.

Each pJ224 plasmid is digested with Sma1 and Kpn1 per the manufacturer's suggested protocol (New England Biolabs, Ipswich, Mass.). The DNA from each reaction is run on an agrose gel, and the appropriate sized bands (for D4E1 approximately 320 bp, for pro-thionin approximately 520 bp, and chimera approximately 600 bp) are excised and then purified using a gel purification kit (Qiagen, Valencia, Calif.). The purified DNA (desired polynucleotide) is then ligated to binary vector pBINPLUS/ARS with T4 ligase (Promega Corp., Madison, Wis.) such that the desired polynucleotide is operably linked upstream (5') to a double CaMV 35S promoter (D35S) and downstream (3') to Nos terminator sequence (Nos-t). As seen in FIG. 2, the pBINPLUS/ARS vector also contains, upstream of the D35S promoter, the Ubi3 promoter (Ubi3-p) operably linked to neomycin phosphotransferase gene (NPTII) which confers kanamycin resistance, which is then operably linked to Ubi3 terminator (Ubi3-t). In FIG. 2, thin arrows indicate the location of PCR primers to confirm DNA integration located between D35S promoter and nos terminator regions. Thick arrow heads indicate the location of primers for RT-PCR and RT-qPCR in target genes and nos terminator regions, respectively.

The three separate ligation reactions are used, individually, to transform *E. coli* TOPO10 competent cells (Invitrogen, Carlsbad, Calif.). Transformed *E. coli* are streaked on plates, and positive bacterial clones are determined by colony PCR, followed by plasmid isolation, and sequencing to confirm the presence of plasmids containing the desired sequences. The binary vectors carrying DNA encoding the desired peptides are introduced into *A. tumefaciens* EHA105 by electroporation. The binary vector pBINPLUS/ARS carrying GUS (β-D-glucuronidase) is also introduced into *A. tumefaciens* EHA105 as negative control. Strains and vectors used in this study are listed in Table 4.

TABLE 4

| Plasmids | Relevant characteristics | Source |
|---|---|---|
| pJ224 | Cloning vector, Amp$^r$ | DNA 2.0 |
| pBINPLUS/ARS-26 | Binary vector carrying GUS, Kan$^r$ | USHRL |
| pBINPLUS/ARS-D4E1 | Binary vector carrying D4E1, Kan$^r$ | This study |

TABLE 4-continued

| Plasmids | Relevant characteristics | Source |
|---|---|---|
| pBINPLUS/ARS-thionin | Binary vector carrying optimized thionin*, Kan$^r$ | This study |
| pBINPLUS/ARS-chimera | Binary vector carrying chimeric protein**, Kan$^r$ | This study |

*contains DNA encoding optimized pro-thionin
**contains DNA encoding optimized pro-thionin - linker 1 - D4E1

Transformation of *N. benthamiana is* performed using the *Agrobacterium*-mediated leaf disk transformation method (Krugel, et al., *Chemoecology* 12:177-183 (2002)). Leaf disks are cultured on Murashige and Skoog (MS) medium with addition of 6-benzylaminopurine at 1 mg/L, 0.1 mg/L naphthaleneacetic acid (NAA), 150 mg/L kanamycin (kan), and 200 mg/L cefotaxime. The kan-resistant plants are selected and rooted in MS medium containing NAA at 0.1 mg/L, 100 mg/L kan and 100 mg/L cefotaxime. The rooted plants are potted in a commercial soil mix for further test in a controlled green house. Most of the genetically altered *N. benthamiana* plants containing optimized pro-thionin (pBIN/ARSPLUS-thionin) are morphologically similar to non-transformed or gus transformed negative control plants except genetically altered *N. benthamiana* line thionin-4 which has long and narrow leaves. Genetically altered *N. benthamiana* plants expressing the chimeric protein (optimized pro-thionin-linker 1-D4E1) are morphologically similar to non-transformed plants.

Over ten kanamycin-resistant transformed *N. benthamiana* plants for each plasmid used for transformation (pBINPLUS/ARS-26, pBINPLUS/ARS-D4E1, pBINPLUS/ARS-thionin, and pBINPLUS/ARS-chimera) are obtained. Six plants for each group are selected for further analysis. To test if the T-DNA region is integrated into the *N. benthamiana* genome, primers are designed to span from the D35S region to Nos terminator region. DNA from each genetically altered plant is individually isolated with plant DNeasy Plant kits (Qiagen, Valencia, Calif.) according to manufacturer's suggested protocol. The D35S promoter primer is 5'-GACGCACAATCCCACTATCC-3' (SEQ ID NO: 46); the Nos terminator primer is 5'-TTTGCGCGCTATATTTTGTTT-3' (SEQ ID NO: 47). The isolated plant genomic DNA is amplified using Taq polymerase (Epicenter, Madison, Wis.) and these primers. The PCR reaction conditions are denature 95° C. for 3 minutes and then 32 cycles of 95° C. for 30 seconds to denature, 53° C. for 30 seconds to anneal, and 72° C. for 1 minute for extension. The PCR products are run on 1% agrose gel and stained with ethidium bromide. The expected 350 bp, 500 bp, and 600 bp fragments are observed, respectively, for transgenic lines carrying pBINPLUS/ARS-D4E1, pBINPLUS/ARS-thionin, or pBINPLUS/ARS-chimera. Meanwhile, a 2,000 bp band is present in gus transformed control plant carrying pBINPLUS/ARS-26.

RT-PCR is performed on the genetically altered *N. benthamiana* plants to assess the expression levels of the heterologous DNA. Trizol reagent is used for RNA extraction according to the manufacture's instruction (Sigma-Aldrich, St. Louis, Mo.). Total RNA is quantified using Nanodrop (Thermo Fisher Scientific, Wilmington, Del.) and is treated with RQ1 RNase-free DNase from Promega Corp (Madison, Wis.). DNase-treated RNA (~1.5 μg) is used to synthesize first-strand cDNA with 0.5 μg of oligo (dT) primer and 1 μL of SuperScript® III reverse transcriptase in a 20 μL reaction (Invitrogen, Carlsbad, Calif.). A negative control without the reverse transcriptase is performed to verify the absence of genomic DNA contamination. PCR is performed as described above with cDNA as template and 26 cycles for all genetically altered lines [optimized pro-thionin-linker 1-D4E1 (pBINPLUS/ARS-chimera); optimized pro-thionin (pBINPLUS/ARS-thionin), and D4E1 (pBINPLUS/ARS-D4E1)]. However, after 26 cycles of RT-PCR with genetically altered *N. benthamiana* plant lines carrying the optimized pro-thionin-linker 1-D4E1 (pBINPLUS/ARS-chimera), no band or only a very faint band is amplified. So, RT-PCR is performed with 32 cycles in the optimized pro-thionin-linker 1-D4E1 genetically altered *N. benthamiana* plants (pBINPLUS/ARS-chimera).

Figure 3B:
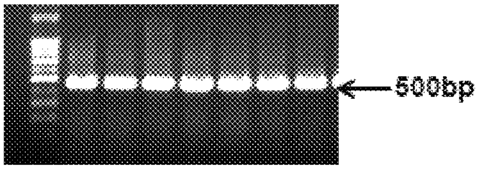

FIG. 3A and FIG. 3B show two gels loaded with the 32 cycles RT-PCR amplification of total RNA from six genetically altered *N. benthamiana* plants (lanes 2, 6, A, B, C, and D) expressing the heterologous chimeric protein (optimized pro-thionin-linker 1-D4E1), molecular weight marker (lane M), and genetically altered *N. benthamiana* plant expressing GUS (lane G). FIG. 3A shows the 300 bp RT-PCR fragment for the chimeric protein. FIG. 3B shows the 500 bp RT-PCR fragment for *N. benthamiana* EF1α (NbEF1α). As evident in FIG. 3A, five genetically altered *N. benthamiana* lines containing the chimeric protein (optimized pro-thionin-linker 1-D4E1; pBINPLUS/ARS-chimera) (chimera 2, 6, A, B and C) show stronger gene expression compare to genetically altered *N. benthamiana* chimera D line. Similar fragments are amplified with NbEF1α forward and reverse primers (SEQ ID NOs: 52 and 53) which serve as a control for cDNA input using the same RT-PCR protocol.

Figure 3C:
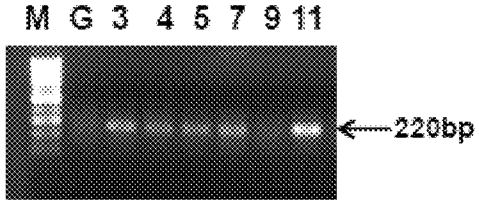
FIG. 3C and FIG. 3D show two gels loaded with the RT-PCR amplification of total RNA from six genetically altered *N. benthamiana* plants (lanes 3, 4, 5, 7, 9, and 11) expressing the heterologous optimized pro-thionin protein, molecular weight marker (lane M), and genetically altered *N. benthamiana* plant expressing GUS (lane G).
Figure 3D:
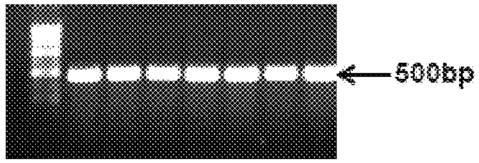

FIG. 3C and FIG. 3D show two gels loaded with the 26 cycles RT-PCR amplification of total RNA from six genetically altered *N. benthamiana* plants (lanes 3, 4, 5, 7, 9, and 11) expressing the heterologous optimized pro-thionin protein, molecular weight marker (lane M), and genetically altered *N. benthamiana* plant expressing GUS (lane G). FIG. 3C shows the 220 bp RT-PCR fragment for optimized pro-thionin. FIG. 3D shows the 500 bp RT-PCR fragment for NbEF1α. As evident in FIG. 3C, five genetically altered *N. benthamiana* optimized thionin lines (thionin 3, 4, 5, 7 and 11) (pBINPLUS/ARS-thionin) show stronger gene expression compared to genetically altered *N. benthamiana* optimized thionin 9 line. Similar products are amplified with NbEF1α forward and reverse primers (SEQ ID NOs: 52 and 53) from these plants using the same RT-PCR protocol.

Figure 3E:
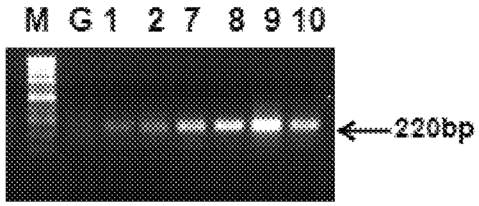
FIG. 3E and FIG. 3F show two gels loaded with the RT-PCR amplification of total RNA from six genetically altered *N. benthamiana* plants (lanes 1, 2, 7, 8, 9, and 10) expressing the heterologous D4E1 protein, molecular weight marker (lane M), and genetically altered *N. benthamiana* plant expressing GUS (lane G).
Figure 3F:
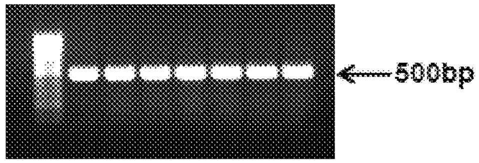

FIG. 3E and FIG. 3F show two gels loaded with the 26 cycles RT-PCR amplification of total RNA from six genetically altered *N. benthamiana* plants (lanes 1, 2, 7, 8, 9, and 10) expressing the heterologous D4E1 protein, molecular weight marker (lane M), and genetically altered plant expressing GUS (lane G). FIG. 3E shows the 220 bp RT-PCR fragment for D4E1. FIG. 3F shows the 500 bp RT-PCR fragment for NbEF1α. Again as evident in FIG. 3E, D4E1 gene expression varies in different genetically altered *N. benthamiana* lines. Strong PCR amplification is observed in genetically altered *N. benthamiana* D4E1 line 8 and genetically altered *N. benthamiana* D4E1 line 9; in contrast only a faint signal is seen for genetically altered *N. benthamiana* D4E1 line 1 and genetically altered *N. benthamiana* D4E1 line 2.

To further compare the gene expression level in these genetically altered *N. benthamiana* lines, RT-qPCR is used to determined RNA abundance against internal control, NbEF1α. RT-qPCR is performed with Bright Green PCR Master Mix (Sigma-Aldrich, St. Louis, Mo.) in triplicate using an ABI 7500 thermal cycler (Applied Biosystems, Foster City, Calif.). Each 25 μL amplification reaction contains 12.5 μL of Bright Green PCR Master Mix, 250 nM of each forward primer and reverse primer, and 2.0 μL of 1:10 diluted cDNA template. The following protocol is used: 95° C. for 2 minutes, 40 cycles of 30 seconds for denaturation at 95° C. and 30 seconds for extension at 60° C. For D4E1 *N. benthamiana* transformants (pBINPLUS/ARS-D4E1), forward primer is 5'-CAAGGTGAGGTTGAGAGCTAAG-3' (SEQ ID NO: 48) and reverse primer is 5'-TCCTAGTTTGCGCGCTATATTT-3' (SEQ ID NO: 49). For optimized pro-thionin *N. benthamiana* transformants (pBINPLUS/ARS-thionin) and chimeric protein optimized pro-thionin-linker 1-D4E1 transformants (pBINPLUS/ARS-chimera) forward primer is 5'-TTTCGCCGTAGATGCAGATG-3' (SEQ ID NO: 50), and reverse primer is 5'-TCCTAGTTTGCGCGCTATATTT-3' (SEQ ID NO: 51). NbEF1α is amplified and used to normalize the values as an internal control using forward primer 5'-GACCACTGAAGTTGGATCTGTTG-3' (SEQ ID NO: 52) and reverse primer 5'-TAGCACCAGTTGGGTCCTTCTT-3' (SEQ ID NO: 53). To compare the transcript levels, a ratio of relative gene expression is calculated from the $2^{\Delta C}$ values of a sample versus a reference sample which has lowest $2^{\Delta C}$ in the tested samples. $\Delta CT = CT$ (target gene)−CT (internal control). The qPCR reactions are performed in triplicate and repeated twice times with similar results. RNA abundance varies between different genetically altered lines and within each group of genetically altered lines.

Figure 4A:
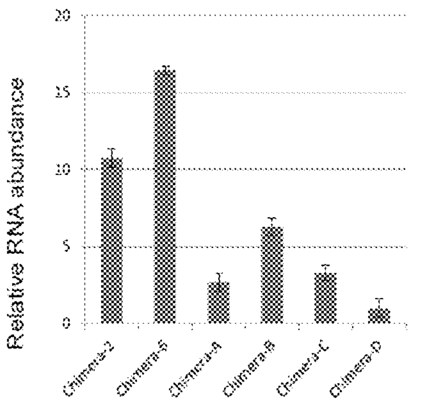
FIG. 4A, FIG. 4B, FIG. 4C show quantitation analysis of RNA levels in different genetically altered *N. benthamiana* lines: chimeric protein optimized pro-thionin-linker 1-D4E1 (FIG. 4A), optimized pro-thinion (FIG. 4B), and D4E1 (FIG. 4C). RT-qPCR is performed to compare gene expression level of the independent genetically altered *N. benthamiana* lines. Relative gene expression of target gene is normalized to the expression of the NbEF1α.
Figure 4C:
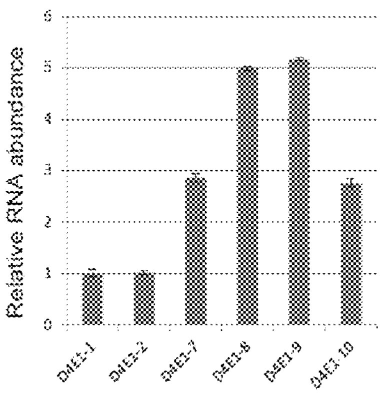
Figure 4B:
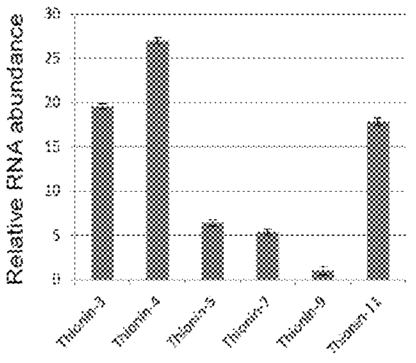

Genetically altered *N. benthamiana* line chimera 6 (optimized pro-thionin-linker 1-D4E1; pBIN/ARSPLUS-chimera) has the highest level of gene expression compare to other genetically altered *N. benthamiana* chimera lines (FIG. 4A). Genetically altered *N. benthamiana* line thionin-4 has over 25 fold expression compared to genetically altered *N. benthamiana* line thionin-9. Genetically altered *N. benthamiana* lines thionin-3 and thionin-11 also shows relatively high gene expression (FIG. 4B). For D4E1, genetically altered *N. benthamiana* lines D4E1-8 and D4E1-9 show higher expression levels compared to other genetically altered *N. benthamiana* D4E1 lines (FIG. 4C).

Example 2 Pathogenicity Assays with Genetically Altered *N. benthamiana*

*P. syringae* ssp. *tabaci* can cause wildfire and angular leaf spot on *N. benthamiana* plants. *P. syringae* ssp. *tabaci* strains that produce the toxin calledas tabtoxinin-β-lactam cause wildfire disease; in contrast, strains that do not produce the toxin produce only angular leaf spot symptoms (Stover, et al. (2013)). Typically wildfire disease is characterized by small brown or black lesions surrounded by chlorotic halos caused by the toxin's mechanism of action. The angular leaf spot is characterized as larger brown or black lesions without chlorotic halos and has angular margins. The *P. syringae* ssp. *tabaci* producing only angular leaf spots symptoms is used in this example.

*P. syringae* ssp. *tabaci* are obtained from Florida Department of Agriculture and Consumer Services. Overnight cultures of *P. syringae* ssp. *tabaci* are centrifuged and diluted to the following concentration in sterile distilled water. Dilutions of $10^2$, $10^3$, $10^4$, $10^5$ and $10^6$ CFU/ml are determined by the standard plate-dilution method (Huang, et al. (1997)). Two leaves of each plant are inoculated with each of the five bacterial inoculum level. The bacterial suspensions are infiltrated from the abaxial side into leaves of the genetically altered *N. benthamiana* plants (D4E1, optimized pro-thionin, optimized pro-thionin-linker 1-D4E1 (chimeric protein), and GUS (negative control)) using a syringe. Inoculated plants are incubated for 14 days. Disease development is scored and photographed. The experiment is repeated three times with similar results.

Yellowing or necrotic lesions are first observed 6 day post infiltration (dpi). Symptoms continue to develop through the 14 days evaluation period. On 14 dpi, the gus transformed *N. benthamiana* lines (negative control) show brown necrosis lesion at the concentration of $10^6$ CFU/ml and yellowing and many brown lesion spots at $10^3$-$10^5$ CFU/ml (see Table 5). Genetically altered *N. benthamiana* lines expressing optimized thionin (optimized pro-thionin) show remarkable resistance with only slight necrosis at the highest infiltration level of $10^6$ CFU/ml. A few lesion spots are observed on all genetically altered *N. benthamiana* lines expressing optimized thionin (see Table 5). Remarkably, genetically altered *N. benthamiana* line 3 expressing optimized thionin only shows slight necrosis on the edge of the infiltrated zone with infiltration at $10^6$ CFU/ml while a few small necrosis lesions are observed with infiltration at $10^3$-$10^5$ CFU/ml. Genetically altered *N. benthamiana* lines expressing the chimera (optimized pro-thionin-linker 1-D4E1) show variation for disease development. Genetically altered *N. benthamiana* lines 2, 6 and B expressing chimera show less necrosis development. However genetically altered *N. benthamiana* lines A and F expressing the chimera only show moderate resistance compare to the negative controls. At low infiltration levels ($10^4$, $10^3$ and $10^2$ CFU/ml), a few necrosis spots are observed (see Table 5). Genetically altered *N. benthamiana* lines expressing D4E1 (D4E1) only show slightly less necrosis compared to gus transformed *N. benthamiana* lines (negative control) at low infiltration concentration of $10^3$ and $10^2$ CFU/ml (see Table 5). These results demonstrate that genetically altered *N. benthamiana* plants expressing optimized thionin or a chimeric protein of optimized thionin-linker 1-D4E1 significantly reduce infection caused by *P. syringae* ssp. *tabaci*, however genetically altered *N. benthamiana* plants expressing D4E1 had only slightly increased resistance to *P. syringae* ssp. *tabaci*.

TABLE 5

| Genetically altered | Infiltration Concentration (CFU/ml) | | | | |
|---|---|---|---|---|---|
| *N. benthamiana* line | $10^2$ | $10^3$ | $10^4$ | $10^5$ | $10^6$ |
| GUS-1 (negative) | 15 | 26 | $N^-$ | $N^-$ | N |
| GUS-2 (negative) | 5 | 22 | $N^-$ | $N^-$ | N |
| Chimera-2 | 0 | 0 | 0 | 3 | $N^-$ |
| Chimera-6 | 0 | 0 | 2 | 4 | $N^-$ |
| Chimera-A | 2 | 10 | 15 | 27 | N |
| Chimera-B | 0 | 0 | 4 | 13 | $N^-$ |
| Chimera-C | 0 | 3 | 8 | 32 | $N^-$ |
| Chimera-D | 0 | 19 | 33 | $N^-$ | N |
| Thionin-3 | 0 | 1 | 1 | 2 | $N^-$ |
| Thionin-4 | 0 | 2 | 4 | 11 | $N^-$ |
| Thionin-5 | 0 | 3 | 17 | 28 | $N^-$ |
| Thionin-7 | 0 | 2 | 11 | 45 | $N^-$ |
| Thionin-9 | 0 | 3 | 6 | 18 | $N^-$ |
| Thionin-11 | 0 | 2 | 3 | 9 | $N^-$ |
| D4E1-1 | 0 | 8 | 38 | $N^-$ | N |
| D4E1-2 | 2 | 12 | 44 | $N^-$ | N |
| D4E1-7 | 0 | 6 | 32 | $N^-$ | N |
| D4E1-8 | 0 | 6 | 26 | $N^-$ | N |
| D4E1-9 | 0 | 8 | 19 | $N^-$ | N |
| D4E1-10 | 0 | 7 | 35 | $N^-$ | N |

"0" indicates no necrotic lesion observed.

A digit other than "0" indicates the average number of small spot lesions per infiltration site (means of four infiltration sites).

$N^-$ indicates necrosis development.

N indicates brown necrosis lesions.

Example 3 Generation of Genetically Altered Orange Trees

Three sets of genetically altered orange plants are generated using the polynucleotides described above and chemically synthesized by DNA 2.0 (Menlo Park, Calif.). One polynucleotide (SEQ ID NO: 1) encodes for D4E1 (SEQ ID NO: 2). The second polynucleotide (SEQ ID NO: 5) encodes for optimized pro-thionin (SEQ ID NO: 6) which, during translation of mRNA into the protein or during post-translation modification, the signal sequence amino acids (SEQ ID NO: 12) are removed to generate optimized thionin (SEQ ID NO: 14). The third polynucleotide (SEQ ID NO: 7) encodes the chimeric protein, optimized pro-thionin-linker 1-D4E1 (SEQ ID NO: 8) which, during translation of mRNA into the peptide or during post-translation modification, the signal sequence amino acids (SEQ ID NO: 12) are removed to generate the chimeric protein, optimized thionin-linker 1-D4E1 (SEQ ID NO: 18). As discussed in Example 1 above, each DNA sequence contains additional nucleotides at the 5' end and 3' end to generate recognition sites for restriction endonucleases Sma1 and Kpn1, respectively (see SEQ ID NO: 43 (D4E1), SEQ ID NO: 44 (optimized pro-thionin), and SEQ ID NO: 45 (optimized pro-thionin-linker 1-D4E1)). The pJ244 plasmids containing these polynucleotides are digested with Sma1 and Kpn1 using the recommended protocol provided by supplier. (New England Biolabs, Ipswich, Mass.) For each construct, the digested DNA is run on an agrose gel, and the desired DNA band (approximately 320 bp for D4E1; approximately 520 bp for optimized thionin; and approximately 600 bp for chimeric protein) is excised and purified. The plasmid pUSHRL-15 is also digested with Sma1 and Kpn1 using manufacturer's recommended protocol. Then purified polynucleotide encoding each desired polypeptide are ligated with the Sma1, Kpn1 digested pUSHRL-15 in form pUSHRL-15D4E1 (encoding D4E1), pUSHRL-15thionin (encoding pro-thionin), and pUSHRL-15chimeric protein (encoding optimized pro-thionin-linker 1-D4E1), respectively. Similar to the pBINPLUS/ARS expression vector described in Example 1 above, pUSHRL expression vector contains D35S promoter upstream of (5') and operably linked to the ligated desired polynucleotide, and Nos-t downstream of (3') and operably linked to the ligated desired polynucleotides. The pUSHRL expression vector also contains Ubi3-p operably linked to NPTII which confers kanamycin resistance, which is then operably linked to Ubi3-t, all upstream of the D35S.

Figure 5A:
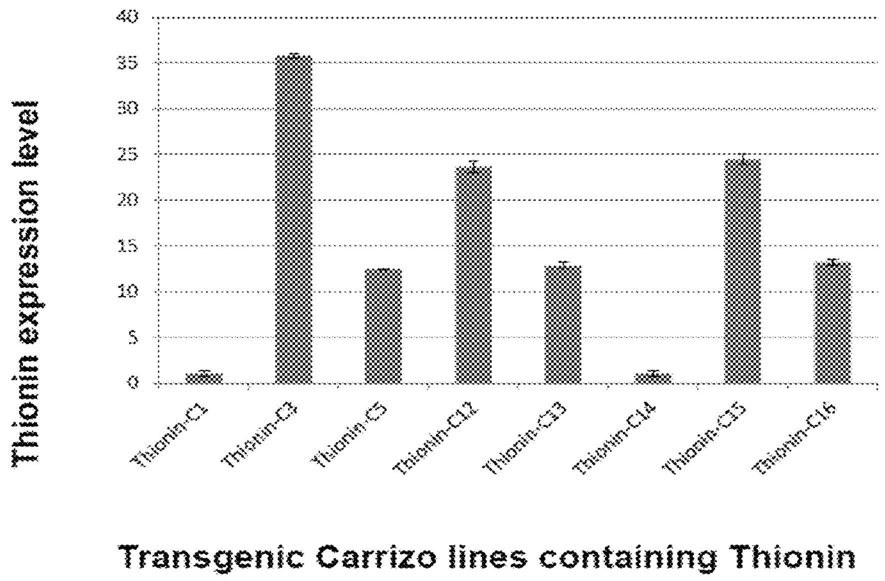
FIG. 5A illustrates the relative gene expression levels for optimized pro-thionin in eight genetically altered Carrizo lines using RT-qPCR.
Figure 5B:
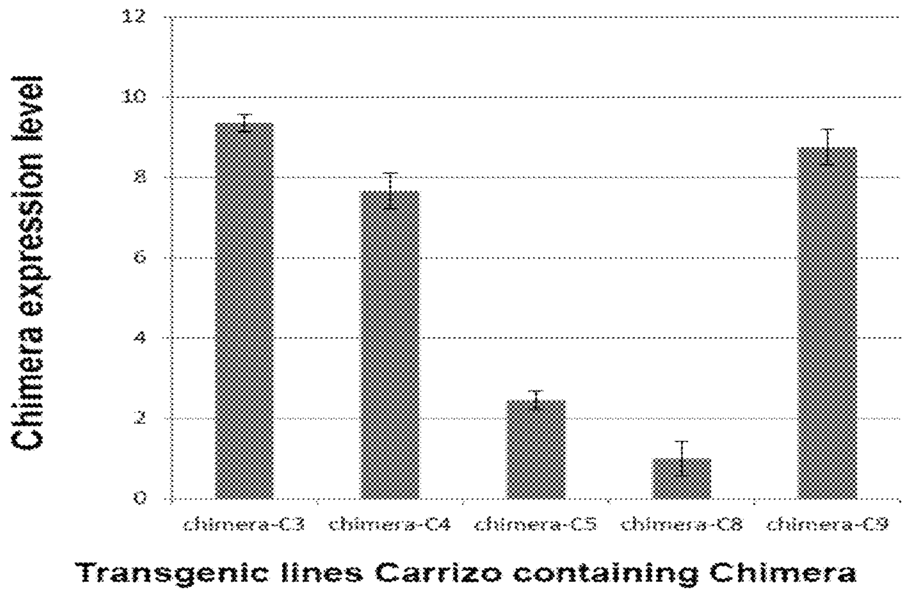
FIG. 5B illustrates the gene expression levels for chimeric protein (optimized pro-thionin-linker 1-D4E1) in five genetically altered Carrizo lines using RT-qPCR.
Figure 5C:
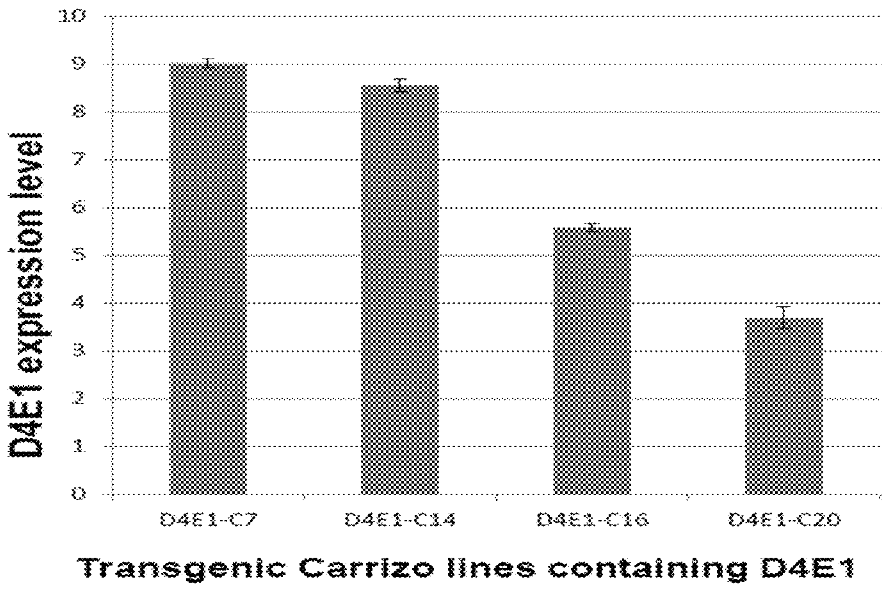
FIG. 5C illustrates the gene expression levels for D4E1 protein in four genetically altered Carrizo lines using RT-qPCR.

Each of pUSHRL-15D4E1, pUSHRL-15thionin, and pUSHRL-15chimeric protein are individually introduced into *Agrobacterium tumefaciens* strain EHA 105 by electroporation, and the resulting recombinant bacteria are used for the transformation of citrus (Carrizo variety (*C. sinensis*× *P. trifoliata*)). The transformation protocol essentially follows Orbovic and Grosser (*Citrus Methods in Molecular Biology* 344:177-189 (2006)) using epicotyl explants tissues that are suspended in a solution of *A. tumefaciens* and plated on selective media containing kanamycin. Kanamycin-resistant plants are selected and rooted in MS medium containing NAA at 0.1 mg/L, 100 mg/L kan and 100 mg/L cefotaxime. Regenerated plantlets are rooted in-vitro and then established in the greenhouse ex-vitro in commercial soil mix. Plants from each transformation are selected for RT-PCR and Southern blot assays to confirm transformation, using the same primers and protocols as described above in Example 1. FIG. 5A illustrates the relative gene expression levels for optimized thionin in eight genetically altered Carrizo lines using RT-qPCR. FIG. 5B illustrates the relative gene expression levels for chimeric protein in five genetically altered Carrizo lines using RT-qPCR. FIG. 5C illustrates the relative gene expression levels for D4E1 protein in four genetically altered Carrizo lines using RT-qPCR.

Example 4 Canker Pathogenicity Assays with Genetically Altered Carrizo Citrus To challenge genetically altered Carrizo, overnight cultures of *Xanthomonas citri* strain 3213 are centrifuged and diluted to $OD_{600}$ of 0.3 with sterile distilled water and further diluted to $10^4$, $10^5$, $10^{6'}$ and $10^7$ CFU/ml, using standard plate-dilution method. (Huang, et al. (1997)) Two leaves of each plant are inoculated with each of the four bacterial inoculum level. The bacterial suspensions are infiltrated from the abaxial side into leaves of the genetically altered Carrizo plants using a syringe. Seven genetically altered plants expressing the chimeric protein, nine genetically altered plants expressing optimized thionin, and four genetically altered plants expressing D4E1 are inoculated, along with two negative control plants. Inoculated plants are incubated for 10 days, and then the disease development is scored and photographed. The pathogenicity assay is repeated three times with similar results. Results are presented in Table 6, below.

TABLE 6

| | Bacterial Infiltration Level (CFU/ml) | | | |
|---|---|---|---|---|
| Transgenic Plant Line | $10^4$ | $10^5$ | $10^6$ | $10^7$ |
| Neg. Control 1 | ++ | +++ | +++++ | +++++ |
| Neg. Control 2 | ++ | +++ | +++++ | +++++ |
| Chimera-C3 | +/− | + | +++ | +++++ |
| Chimera-C4 | − | +/− | ++ | +++++ |
| Chimera-C6 | − | − | +/− | +++++ |
| Chimera-C9 | − | − | +/− | ++++ |
| Chimera-C23 | +/− | + | +++ | +++++ |
| Chimera-C24 | +/− | + | +++ | +++++ |
| Chimera-C29 | − | + | +++ | +++++ |
| Optimized Thinion-C1 | − | +/− | + | ++++ |
| Optimized Thinion-C3 | +/− | + | +++ | +++++ |
| Optimized Thinion-C4 | +/− | + | +++ | +++++ |
| Optimized Thinion-C12 | − | − | + | ++++ |
| Optimized Thinion-C13 | − | − | +/− | ++++ |
| Optimized Thinion-C14 | − | − | +/− | ++++ |
| Optimized Thinion-C31 | − | − | ++ | ++++ |
| Optimized Thinion-C34 | − | − | + | ++++ |
| Optimized Thinion-C41 | − | − | +/− | ++++ |
| D4E1-C3 | + | ++ | ++++ | +++++ |
| D4E1-C10 | ++ | +++ | +++++ | +++++ |
| D4E1-C20 | + | ++ | +++ | +++++ |
| D4E1-C22 | + | ++ | ++++ | +++++ |

− indicates no canker observed

+ indicates canker observed (the number of "+" indicates severity of disease observed with "+++++" being highest)

Figure 6:
FIG. 6 shows genetically altered orange plants expressing either optimized pro-thionin-linker 1-D4E1 or only D4E1 and negative control plants (nontransformed) after exposure to *X. citri.*

Next, genetically altered Carrizo plants (expressing either optimized pro-thionin-linker 1-D4E1 or D4E1) are propagated as multiple trees of each type alongside non-genetically altered (negative control) plants. All plants are exposed to high ambient levels of *Xanthomonas citri* in a greenhouse containing infected citrus trees. After three weeks, disease development is scored and photographed. The non-genetically altered plants (negative control) all display signs of severe disease. Many genetically altered Carrizo plants containing only D4E1 display severe disease, however a few appear somewhat healthy. In contrast, almost all of the genetically altered Carrizo plants expressing optimized pro-thionin-linker 1-D4E1 are healthy. A few plants display mild symptoms of canker. See FIG. 6.

Example 5 HLB Pathogenicity Assays with Genetically Altered Carrizo Citrus

To assess the chimeric protein's efficacy in killing CLas in genetically altered Carrizo citrus plants, genetically altered budwood and non-genetically altered budwood are micrografted to small plants of standard citrus rootstocks using standard protocols known to one of ordinary skill in the art. The budwood are obtained from the genetically altered Carrizo citrus plants produced in Example 3 above which exhibit the best protection against *X. citri* in Example 4 above. Ten grafted citrus plants containing budwood from genetically altered plants lines expressing D4E1 or optimized pro-thionin or the chimeric protein (optimized pro-thionin-linker 1-D4E1) are used in each group along with negative control group (non-genetically altered budwood grafted plants). Each group is replicated. After the graft union heals and the grafted plants have 3 to 5 leaves, the grafted plants are placed in a no-choice Asian citrus psyllid (ACP) feeding trial on a lab bench at room temperature (~23° C.) under artificial lighting. Each scion/rootstock combination are exposed to CLas infected ACP for 2 weeks, after which the psyllids are removed. At 3, 6, 9, and 12 weeks after ACP exposure, the entire plant (leaves, stems, and roots) are sacrificed, weighed and completely processed for qPCR analysis of CLas titer. Groups of similarly micrografted plants are maintained in the greenhouse for up to 2 years and then are planted in the field, monitoring symptoms and growth with periodic leaf sampling for CLas titer. All samples are frozen until processed. DNA is extracted from a subsample (100 mg) of frozen tissue (leaf, stem, and root) using Qiagen DNeasy plant mini kit (Gaithersburg, Md.) using manufacturer's recommended protocols. To determine CLas titer levels real-time qPCR is performed, in triplicate, on ABI 7500 real time PCR thermal cycler (Applied Biosystems, Foster City, Calif.) with Bright Green PCR Master Mix (Sigma-Aldrich, St. Louis, Mo.). Each 25 μL amplification reaction contains 12.5 μL of Bright Green PCR Master Mix, 250 nM of each forward primer and reverse primer, and 2.0 μL (about 100 ng) DNA template.

The primers used for the real-time qPCR are specific to 16s rDNA for CLas detection (CLas Long=LL): USHRL-LL-F 5'-CTTACCAGCCCTTGACATGTATAGG-3' (forward primer, SEQ ID NO: 63) and USHRL-LL-R 5'-TCCCTATAAAGTACCCAACATCTAGGTAAA-3' (reverse primer, SEQ ID NO: 64) or to citrus dehydrin (CD-F 5'-TGAGTACGAGCCGAGTGTTG-3' (forward primer, SEQ ID NO: 65) and CD-R 5'-AAAACTTCACCGATCCACCAG-3' (reverse primer, SEQ ID NO: 66)). Citrus dehydrin is used as an internal reference to quantify the number of plant genomes per reaction. The cycle parameters are 40 cycles of 30 seconds for denaturation at 95° C. and 30 seconds for extension at 60° C., with a melt curve analysis (to verify product identity) as described above in Example 1. Genome equivalents for CLas and citrus dehydrin are calculated based on standard curves developed with each primer pair and serial dilutions of the target DNA on plasmids of known copy number in a background of clean citrus DNA. Calculations are based on 3 copies of rDNA target per genome of CLas and 2 copies of citrus dehydrin per genome. qPCR results comparing levels of CLas, and non-parametric symptom data are analyzed using the non-parametric Kruskal-Wallis test (SAS, Cary, N.C.). Growth data are analyzed using ANOVA. Standard growth measurements, CLas titer levels, and disease ratings provide an indication of the potential for commercially viable growth in the presence of endemic HLB. After the trees reach fruit bearing age, crop yields will be evaluated to determine the economic potential of HLB-resistance in the genetically altered grafted citrus plants as compared to standard cultivars.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

We, the inventors, claim as follows:

1. A genetically altered plant, a part or progeny thereof comprising a promoter operably linked to a polynucleotide encoding a chimeric protein comprising SEQ ID NO: 8 or SEQ ID NO: 18, wherein said genetically altered plant or parts thereof and its progeny produce said chimeric protein, and wherein said genetically altered plant, part or progeny thereof is more resistant to *Xanthomonas citri* ssp. *citri* compared to a wild-type plant's resistance to *X. citri* ssp. *citri*.

2. A method for constructing a genetically altered plant or part thereof having increased resistance to *Xanthomonas citri* ssp. *citri* compared to a non-genetically altered plant or part thereof, the method comprising:

(i) introducing a polynucleotide encoding a chimeric protein into a plant or part thereof to produce a genetically altered plant or part thereof, wherein said chimeric protein comprising a first domain, a second domain, and a third domain, wherein said first domain comprises optimized thionin or optimized pro-thionin, said second domain comprises D4E1 or pro-D4EI, and said third domain comprises a peptide linker; wherein said peptide linker separates said first domain from said second domain such that said first domain and said second domain can each fold into its appropriate three-dimensional shape and retains its activity, and wherein said peptide linker ranges in length between three amino acids and approximately forty-four amino acids;

(ii) selecting a genetically altered plant or part thereof that expresses said chimeric protein, wherein said expressed chimeric protein has anti-bacterial activity against *X. citri* ssp. *citri*; wherein said genetically altered plant or part thereof has increased resistance to *X. citri* ssp. *citri* compared to the resistance to *X. citri* ssp. *citri* of said non-genetically altered plant or part thereof; and wherein said optimized thionin comprises the amino acid sequence of SEP ID NO: 14, said optimized pro-thionin comprises the amino acid sequence of SEP ID NO: 6, said D4E1 comprises the amino acid sequence of SEP ID NO: 2, and said pro-D4EI comprises the amino acid of SEP ID NO: 62.

3. The method of claim 2, wherein said introducing said polynucleotide encoding said chimeric protein occurs via introgression or transforming said plant with an expression vector comprising said polynucleotide operably linked to a promoter.

4. The method of claim 2, wherein said optimized thionin or said optimized pro-thionin is located at the amino terminus of said chimeric protein; and wherein said D4E1 is located at the carboxyl terminus of said chimeric protein.

5. The method of claim 2, wherein said D4E1 or said pro-D4E1 is located at the amino terminus of said chimeric protein; and wherein said optimized thionin is located at the carboxyl terminus of said chimeric protein.

6. A method of enhancing a wild-type plant's resistance to canker comprising transforming a cell from said wild-type plant with a polynucleotide encoding a chimeric protein to generate a transformed plant cell; and growing said transformed plant cell to generate a genetically altered plant; wherein said chimeric protein comprises a first domain, a second domain, and a third domain; wherein said first domain comprises optimized thionin or optimized pro-thionin, said second domain comprises D4E1 or pro-D4E1, and said third domain comprises a peptide linker; wherein said peptide linker separates said first domain from said second domain such that said first domain and said second domain can each fold into its appropriate three-dimensional shape and retains its activity; wherein said peptide linker is ranges in length between three amino acids and approximately forty-four amino acids; wherein said genetically altered plant or part thereof produces said chimeric protein; and wherein said chimeric protein kills *Xanthomonas citri* ssp. *citri*; and wherein said genetically altered plant's resistance to said canker is greater than said wild-type plant's resistance to said canker; and wherein said optimized thionin comprises the amino acid sequence of SEQ ID NO: 14, said optimized pro-thionin comprises the amino acid sequence of SEQ ID NO: 6, said D4E1 comprises the amino acid sequence of SEQ ID NO: 2, and said pro-D4E1 comprises the amino acid of SEQ ID NO: 62.

7. The method of claim 6, wherein said optimized thionin or said optimized pro-thionin is located at the amino terminus of said chimeric protein; and wherein said D4E1 is located at the carboxyl terminus of said chimeric protein.

8. The method of claim 6, wherein said D4E1 or said pro-D4E1 is located at the amino terminus of said chimeric protein; and wherein said optimized thionin is located at the carboxyl terminus of said chimeric protein.

9. A genetically altered plant or part thereof produced by the method of claim 2.

10. A genetically altered plant or part thereof produced by the method of claim 6.

11. The method of claim 2, wherein said linker comprises an amino acid sequence selected from the group consisting of SEQ ID NOs: 10, 39, 40, 41, and 42.

12. The method of claim 11, wherein said chimeric protein comprises an amino acid sequence of SEQ ID NO: 8 or SEQ ID NO: 18.

13. A genetically altered plant or part thereof produced by the method of claim 12.

14. The method of claim 6, wherein said linker comprises an amino acid sequence selected from the group consisting of SEQ ID NOs: 10, 39, 40, 41, and 42.

15. The method of claim 14, wherein said chimeric protein comprises an amino acid sequence of SEQ ID NO: 8 or SEQ ID NO: 18.

16. A genetically altered plant or part thereof produced by the method of claim 15.

* * * * *